United States Patent
Chen et al.

(10) Patent No.: US 7,888,504 B2
(45) Date of Patent: Feb. 15, 2011

(54) GLUCOKINASE ACTIVATORS AND METHODS OF USING SAME

(75) Inventors: Sean Chen, Princeton, NJ (US); Peter T. W. Cheng, Princeton, NJ (US); Rebecca A. Smirk, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 708 days.

(21) Appl. No.: 11/769,799

(22) Filed: Jun. 28, 2007

(65) Prior Publication Data

US 2008/0021052 A1 Jan. 24, 2008

Related U.S. Application Data

(60) Provisional application No. 60/818,879, filed on Jul. 6, 2006.

(51) Int. Cl.
C07D 277/34 (2006.01)
C07D 277/36 (2006.01)
C07D 277/38 (2006.01)
C07D 417/12 (2006.01)
C07D 403/12 (2006.01)
A61K 31/427 (2006.01)
A61K 31/506 (2006.01)
A61P 3/10 (2006.01)

(52) U.S. Cl. .............. 544/194; 544/195; 544/319; 514/369; 514/370; 514/269; 514/336; 546/268.1

(58) Field of Classification Search ............. 548/194, 548/195; 514/369, 370; 544/194, 195
See application file for complete search history.

(56) References Cited

U.S. PATENT DOCUMENTS

| | | | | |
|---|---|---|---|---|
| 6,214,852 B1 * | 4/2001 | Kim et al. | | 514/369 |
| 6,262,096 B1 * | 7/2001 | Kim et al. | | 514/369 |
| 6,320,050 B1 | 11/2001 | Bizzarro et al. | | |

FOREIGN PATENT DOCUMENTS

| | | |
|---|---|---|
| WO | WO 00/58293 | 10/2000 |
| WO | WO 02/08209 | 1/2002 |
| WO | WO 02/46173 | 6/2002 |
| WO | WO 03/095438 | 11/2003 |
| WO | WO 2004/072031 | 8/2004 |
| WO | WO 2004/072066 | 8/2004 |
| WO | WO 2005/103021 | 11/2005 |
| WO | WO 2006/016174 | 2/2006 |
| WO | WO 2006/016178 | 2/2006 |
| WO | WO 2006/016194 | 2/2006 |
| WO | WO 2006/058923 | 6/2006 |

OTHER PUBLICATIONS

Cecil Textbook of Medicine, edited by Bennet, J.C., and Plum F., 20th edition, vol. 1, 1004-1010, 1996.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Iynedjian et al., Cell. Mol. Life Sci. 66, 27-42, 2009.*
Printz et al., Endocrinology 146(9):3693-3695, 2002.*
Pal, M., Drug Discovery Today, 14, 784-792, 2009.*
Turner et al., Current Pharmaceutical Design. 2, 209-224, 1996.*
Sugar et al., Diagn. Microbiol. Infect. Dis. 21: 129-133, 1995.*
Snyder et al., J. Med. Liban 48(4): 208-214, 2000. PubMed Anstract provided.*
Fyfe, M. C. T. et al., "Glucokinase activator PSN-GK1 displays enhanced antihyperglycaemic and insulinotropic actions", Diabetologia, 50(6), pp. 1277-1287, (2007).
Guertin, K.R. et al., "Small molecule glucokinase activators as glucose lowering agents: A new paradigm for diabetes therapy", Current Medicinal Chemistry, 13(15), pp. 1839-1843, (2006).
Sarabu, R. et al., "Targeting glucokinase activation for the treatment of type 2 diabetes—A status review", Current Opinion in Drug Discovery and Development, 8(5), pp. 631-637, (2005).

* cited by examiner

Primary Examiner—Venkataraman Balasubramanian
(74) Attorney, Agent, or Firm—Maureen S. Gibbons; Burton Rodney

(57) ABSTRACT

Compounds are provided which are glucokinase activators and thus are useful in treating diabetes and related diseases and have the structure

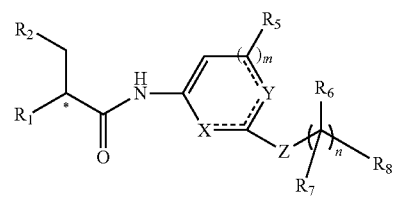

wherein
) in the ring represents one or two double bonds;
$R_1$ is aryl or heteroaryl;
$R_2$ is halogen, cycloalkyl, heterocyclyl, aryl, or heteroaryl;
$R_5$ is as defined herein;
Z is O, S, S(O), S(O)$_2$, or NR$_{5a}$;
X is S, O, N, NR$_3$, or CR$_3$;
Y is NCR$_4$ or N$_4$;
$R_3$, $R_4$, and $R_5$ are as defined herein;
$R_8$ is aryl or heteroaryl;
$R_6$ and $R_7$ are independently H, halogen, or alkyl;
m is 0 or 1; and
n is 0 to 3,
or a pharmaceutically acceptable salt thereof.

A method for treating diabetes and related diseases employing the above compounds is also provided.

18 Claims, No Drawings

GLUCOKINASE ACTIVATORS AND METHODS OF USING SAME

This application claims a benefit of priority from U.S. Provisional Application No. 60/818,879, filed Jul. 6, 2006, the entire disclosure of which is herein incorporated by reference.

FIELD OF THE INVENTION

The present invention relates to novel compounds which are activators of the enzyme glucokinase and thus are useful in treating diabetes, and to a method for treating diabetes, especially Type II diabetes, using such compounds.

BACKGROUND OF THE INVENTION

The enzyme glucokinase (GK), which is mainly found in pancreatic β-cells and liver parenchymal cells, catalyzes the conversion of glucose to glucose-6-phosphate, which is the first step in the metabolism of glucose. Glucokinase is also a rate-controlling enzyme for glucose metabolism in pancreatic β-cells and liver parenchymal cells, which play an important role in whole-body glucose homeostasis.

Liag, Y. et al., (Biochem. J., 1995, 309:167-173) report the finding that Type II (maturity-onset) diabetes of the young (MODY-2) is caused by loss of function mutations in the glucokinase gene, which suggests that glucokinase also functions as a glucose sensor in humans. Thus, compounds that activate glucokinase and thus increase the sensitivity of the glucokinase sensor system and thereby cause increase in insulin secretion will be useful in the treatment of hyperglycemia and Type II diabetes.

Glucokinase activators have been demonstrated to be effective in enhancing: 1) the effect of glucose on insulin release from isolated rat and human pancreatic islets, and 2) the glucose induction of pancreatic islet glucokinase in isolated cultured rat islets (e.g. Matschinsky, F. M. et al., Diabetes, 2006, 55:1, and ("Glucokinase and Glycemic Disease, from Basics to Novel Therapeutics", published by Karger, 2004; F. M. Matschinsky and M. A. Magnuson, eds., Ch. 6, pp. 360-378). In diabetic animal model studies, glucokinase activators have been demonstrated to stimulate insulin release, enhance glycogen synthesis and reduce hepatic glucose production in pancreatic clamp studies. Importantly, glucokinase activators have been demonstrated to dose-dependently lower blood glucose levels in different standard animal models of type 2 diabetes, such as the ob/ob mouse, db/db mouse and Zucker in acute single-dose studies and also effectively improved the glucose excursion in both normal C57/BL6J and ob/ob mice in oral glucose tolerance tests (e.g. in "Glucokinase and Glycemic Disease, from Basics to Novel Therapeutics", published by Karger, 2004; F. M. Matschinsky and M. A. Magnuson, eds., Ch. 6, pp. 360-378 as well as Fyfe, M. C. et al., Diabetologia, 2007, 50:1277).

Glucokinase activators have also demonstrated antidiabetic efficacy in chronic animal models of type II diabetes. For instance, in a 9-day study in ob/ob mice, a glucokinase activator improved the overall glucose profile while showing comparable antihyperglycemic effects in oral glucose tolerance tests at the beginning and end of the study (Fyfe, M. C. et al., Diabetologia, 2007, 50:1277). In another instance, in a chronic 40-week study, a glucokinase activator prevented the development of hyperglycemia in diet-induced obese mice which were glucose intolerant. The diet-induced obese mice treated with a glucokinase activator showed marked improvement in the glucose excursion in an oral glucose tolerance test at the end of the study relative to the control group ("Glucokinase and Glycemic Disease, from Basics to Novel Therapeutics", published by Karger, 2004; F. M. Matschinsky and M. A. Magnuson, eds., Ch. 6, pp. 360-378).

SUMMARY OF THE INVENTION

In accordance with one aspect of the invention, compounds are provided having the structure I

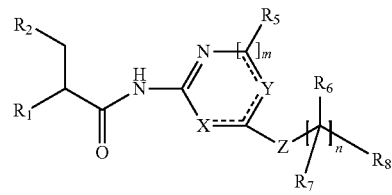

wherein
) in the ring represents one or two double bonds;
$R_1$ is selected from
 aryl, or
 heteroaryl;
$R_2$ is selected from
 cycloalkyl,
 heterocyclyl,
 aryl, or
 heteroaryl;
X is selected from
 S,
 O,
 N,
 $NR_3$, or
 $CR_3$;
Y is selected from
 N,
 $CR_4$, or
 $NR_4$;
Z is selected from
 O,
 S,
 S(O),
 $S(O)_2$, or
 $NR_{5a}$;
$R_3$, $R_4$, and $R_5$ are the same or different and are independently selected from
 H,
 halogen,
 alkyl,
 aryl,
 heteroaryl,
 alkylaryl, or
 alkylheteroaryl;
however, when X is $NR_3$ or Y is $NR_4$, $R_3$ and $R_4$ are not halogen;
$R_{5a}$ is selected from
 H,
 Alkyl, or
 aryl;
$R_6$ and $R_7$ are the same or different and are independently selected from
 hydrogen,
 halogen (preferably F), or
 alkyl;

$R_8$ is selected from
aryl or
heteroaryl;
m is 0 or 1;
n is, 1, 2, or 3;

stereoisomers thereof, a prodrug ester thereof, or a pharmaceutically acceptable salt thereof, with the proviso that
where Z is S, S(O) or S(O)$_2$, then $R_8$ must be substituted with a substituent selected from

1)

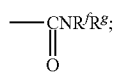

2)

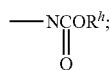

3)

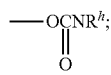

4)

5) alkoxy;
6) tetrazolyl; and
7) —SO$_2$NR$^i$R$^j$;

where R$^f$ and R$^g$ are independently selected from H, alkyl and aryl or R$^f$ and R$^g$ can be taken together with the N atom to which they are attached to form a 3 to 7 membered heterocyclo ring;
R$^h$ is alkyl or aryl; and
R$^i$ and R$^j$ are independently selected from H, alkyl and aryl, provided that at least one of R$^i$ and R$^j$ is other than H.

It will be appreciated that when Z is O or NR$_{5a}$, the R$_8$ group may be substituted with any of the above 1) to 7) groups as well as other substituents disclosed herein.

Examples of moieties of the structure

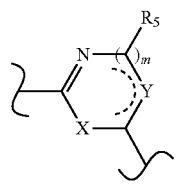

which may be present in the formula I compounds including but are not limited to

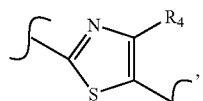

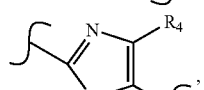

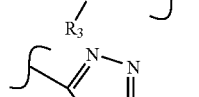

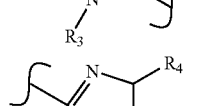

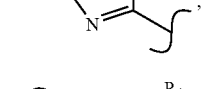

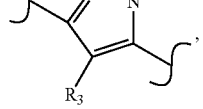

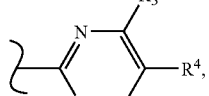

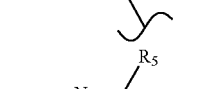

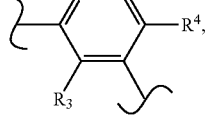

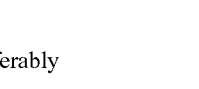

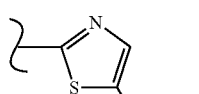

preferably

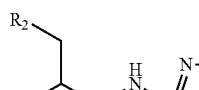

Preferred compounds of the invention have the structure Ia

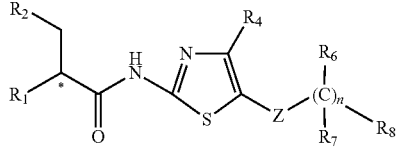

Ia wherein $R_1$, $R_2$, $R_4$, $R_5$, $R_6$, $R_7$, $R_8$, Z, and n are as defined above for compounds of formula I; and
Z is O, S or S(O)$_2$, or Z is O or NR$_{5a}$.

In more preferred compounds of formulas I and Ia of the invention

R$_4$, R$_5$, R$_6$, and R$_7$ are each H;

R$_8$ is phenyl or heteroaryl, either of which is substituted with one or two groups selected from —CONR$^f$R$^g$, $$-\underset{\underset{O}{\|}}{N}COR^h, \quad -O\underset{\underset{O}{\|}}{C}NR^h, \quad -\underset{\underset{O}{\|}}{N}CR^h,$$

alkoxy, tetrazolyl and SO$_2$NR$^i$R$^j$, where Z is O, R$_8$ may be substituted as above and/or with CO$_2$H, CO$_2$alkyl and/or halogen;

R$_1$ is aryl or alkylsulfonylaryl;

R$_2$ is cycloalkyl; and

Z is O, S, or SO$_2$.

In still more preferred compounds of the invention

R$_1$ is alkyl-S(=O)$_2$-phenyl- or cycloalkyl-S(=O)$_2$-phenyl- ;

R$_2$ is cyclopentyl-CH$_2$- or tetrahydropyran-4-yl- ;

Z is S, O, or SO$_2$;

$$-\underset{R_7}{\overset{R_6}{|}}(C)_n-$$

is CH$_2$ or a bond; and

R$_8$ is heteroaryl or phenyl which are substituted with one or two groups selected from —CONR$^f$R$^g$, $$-\underset{\underset{O}{\|}}{N}COR^h, \quad -O\underset{\underset{O}{\|}}{C}NR^h, \quad -\underset{\underset{O}{\|}}{N}CR^h,$$

alkoxy, tetrazolyl and —SO$_2$NR$^i$R$^j$, where Z is O, R$_8$ may be substituted as above and/or with CO$_2$alkyl, CO$_2$H or halogen.

In still more preferred compounds of formula Ia of the invention

R$_1$ is

CH$_3$-S(=O)$_2$-phenyl- ; or cycloalkyl-S(=O)$_2$-phenyl- ;

R$_2$ is cyclopentyl-CH$_2$- or tetrahydropyran-4-yl- ;

R$_3$ is H;
R$_4$ is H;
R$_5$ is H;
X is S;
Y is C;
m is 0;
Z is S, O, or SO$_2$;
n is 0 or 1;

$$-\underset{R_7}{\overset{R_6}{|}}(C)_n-$$

is CH$_2$ or a bond; and

R$_8$ is

[substituted benzamide structures including: 3-methyl-N-methylbenzamide; 2-methyl-4,6-dimethoxypyrimidine; 3-methyl-N-methylbenzamide; 4-methylbenzoic acid; 4-methylbenzoic acid; 3-methylbenzonitrile; 3-methylphenyl-tetrazole; 3-methylphenyl-azetidinyl ketone; and 3-methylphenyl-(3-hydroxyazetidinyl) ketone]

In preferred embodiments of the invention, (1) where Z is SO$_2$, n will be 1, and (2) wherein Z is S, then when R$_5$ and R$_6$ are each hydrogen, R$_8$ will be other than oxazole.

Examples of preferred compounds of the invention include
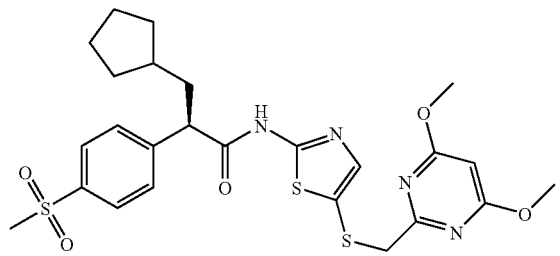
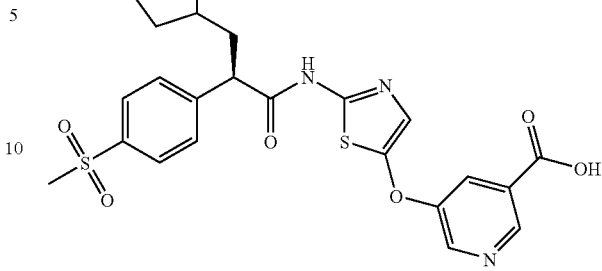
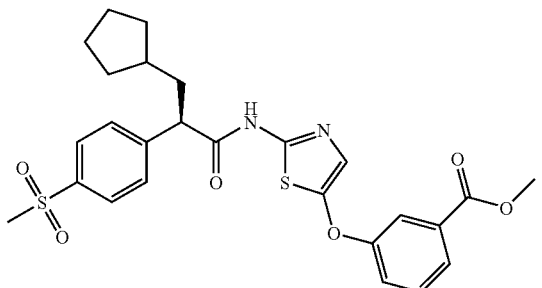
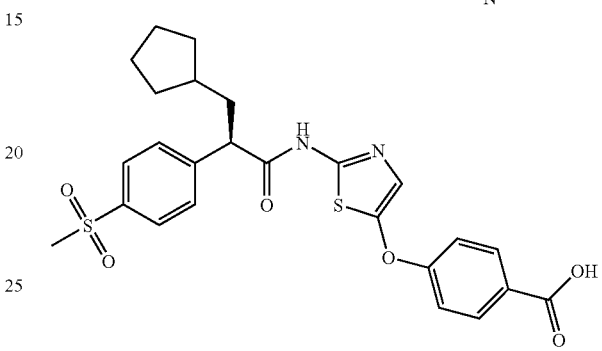
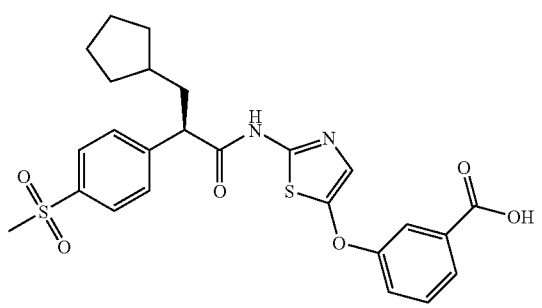
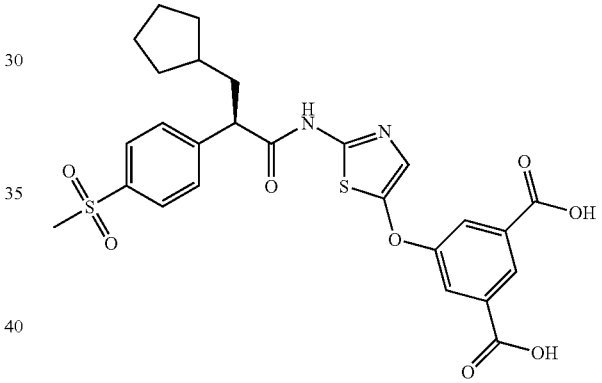
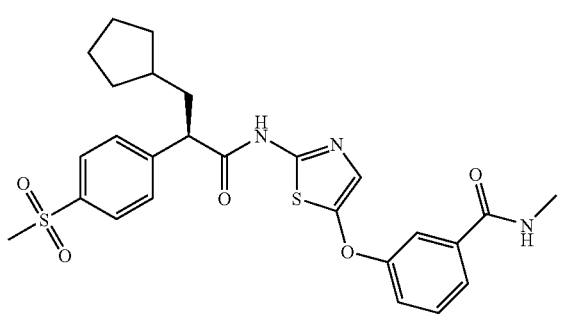
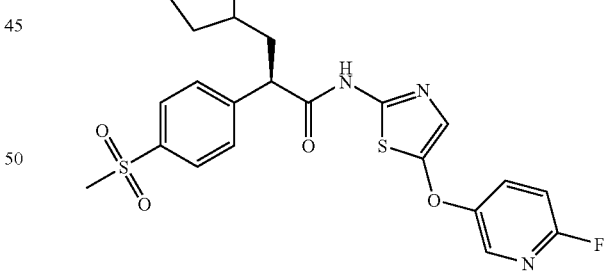
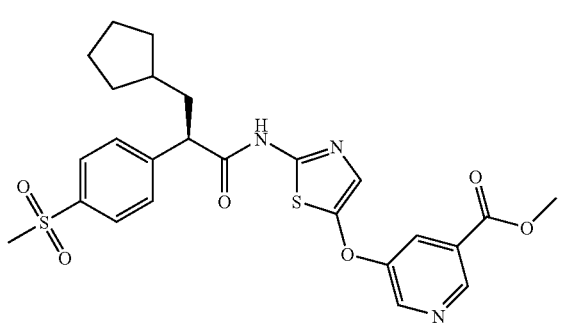
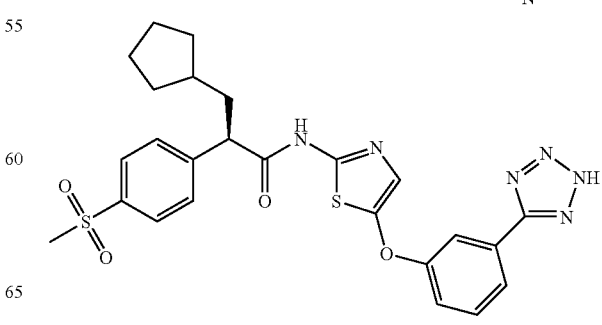

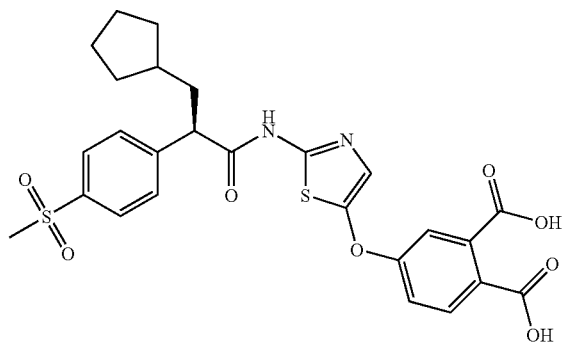

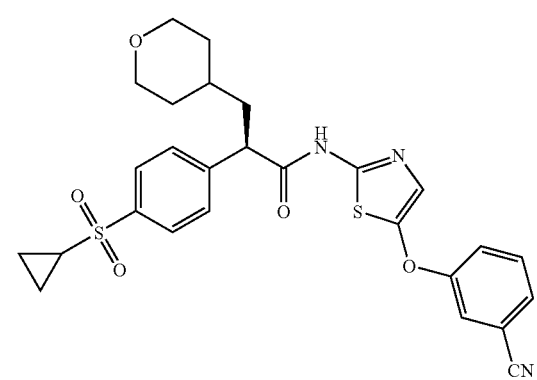

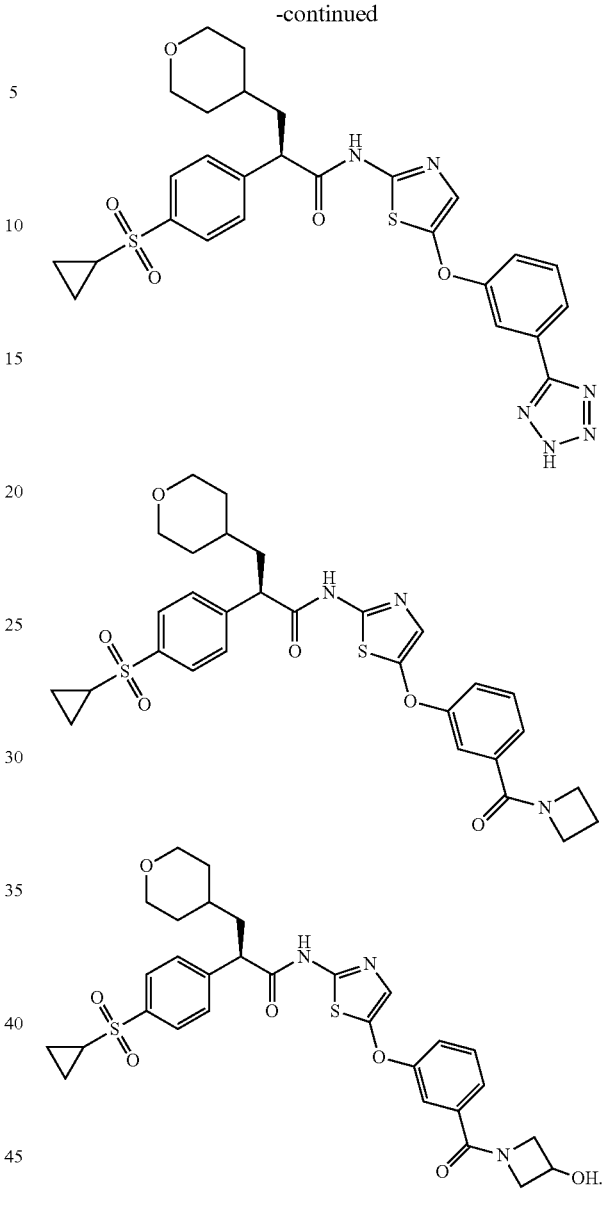

The compounds of the present invention activate or enhance the activity of the enzyme glucokinase. Consequently, the compounds of the present invention may be used in the treatment of multiple diseases or disorders associated with a deficit of glucokinase, such as diabetes and related conditions, microvascular complications associated with diabetes, the macrovascular complications associated with diabetes, cardiovascular diseases, Metabolic Syndrome and its component conditions, and other maladies. Examples of diseases or disorders associated with deficit in activity of the enzyme glucokinase that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

The present invention provides for compounds of formula I, pharmaceutical compositions employing such compounds, and for methods of using such compounds. In particular, the present invention provides a pharmaceutical composition containing a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with deficit in the activity of the enzyme glucokinase, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other therapeutic agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

In another embodiment, compounds of the present invention are selected from the compounds exemplified in the examples.

In another embodiment, the present invention relates to pharmaceutical compositions which include of a therapeutically effective amount of a compound of the present invention, alone or, optionally, in combination with a pharmaceutically acceptable carrier and/or one or more other agent(s).

In another embodiment, the present invention relates to methods of enhancing the activity of the enzyme glucokinase which includes the step of administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with deficit in the activity of the enzyme glucokinase which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the deficit in activity of the enzyme glucokinase that can be prevented, inhibited, or treated according to the present invention include, but are not limited to, are those diseases or disorders set out above.

In another embodiment, the present invention relates to a method for preventing, inhibiting, or treating the progression or onset of diabetes, hyperglycemia, obesity, dyslipidemia, hypertension, and cognitive impairment which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dyslipidemia, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

DETAILED DESCRIPTION OF THE INVENTION

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms, and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "lower alkyl," "alkyl," or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like; such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio, as well as (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}$alkylene$)NR_aR_b$, —$C(=O)NR_a(SO_2)R_b$, —$CO_2(C_{1-4}$alkylene$)NR_aR_b$, —$NR_aC(=O)R_b$, —$NR_aCO_2R_b$, —$NR_a(C_{1-4}$alkylene$)CO_2R_b$, =N—OH, =N—O-alkyl, wherein $R_a$ and $R_b$ are the same or different and are independently selected from hydrogen, alkyl, alkenyl, $CO_2H$, $CO_2$(alkyl), $C_{3-7}$cycloalkyl, phenyl, benzyl, phenylethyl, naphthyl, a 4 to 7 membered heterocyclo, or a 5 to 6 membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of $(C_{1-6})$alkyl, $(C_{2-6})$alkenyl, hydroxy, halogen, cyano, nitro, $CF_3$, $O(C_{1-6}$alkyl$)$, $OCF_3$, $C(=O)H$, $C(=O)(C_{1-6}$alkyl$)$, $CO_2H$, $CO_2$ $(C_{1-6}$ alkyl$)$, $NHCO_2(C_{1-6}$alkyl$)$, —$S(C_{1-6}$alkyl$)$, —$NH_2$, $NH(C_{1-6}$ alkyl$)$, $N(C_{1-6}$alkyl$)_2$, $N(CH_3)_3^+$, $SO_2(C_{1-6}$alkyl$)$, $C(=O)(C_{1-4}$alkylene$)NH_2$, $C(=O)(C_{1-4}$alkylene$)NH$ (alkyl), $C(=O)(C_{1-4}$alkylene$)N(C_{1-4}$alkyl$)_2$, $C_{3-7}$cycloalkyl, phenyl, benzyl, phenylethyl, phenyloxy, benzyloxy, naphthyl, a 4 to 7 membered heterocylo, or a 5 to 6 membered heteroaryl. When a substituted alkyl is substituted with an aryl, heterocyclo, cycloalkyl, or heteroaryl group, said ringed systems are as defined below and thus may have zero, one, two, or three substituents, also as defined below.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

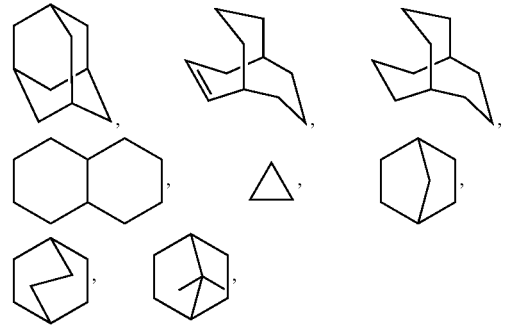

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio, and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

Unless otherwise indicated, the term "aryl" as employed herein alone or as part of another group refers to monocyclic and bicyclic aromatic groups containing 6 to 10 carbons in the ring portion (such as phenyl, biphenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings) for example

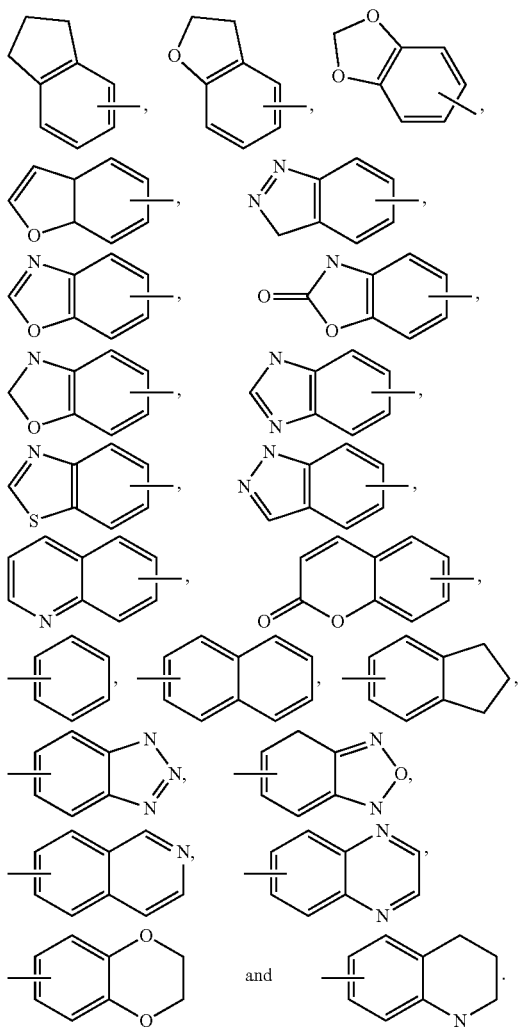

The aryl group may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfon-aminocarbonyl, $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g. cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R_3$ groups or substituents for $R_3$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

The term "acyl" alone or as part of another group refers to a carbonyl group linked to an organic radical, more particularly, the group $C(=O)R_c$, as well as the bivalent groups $-C(=O)-$ or $-C(=O)R_e-$, which are linked to organic radicals. The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The term "heterocyclo" or "heterocyclic" or "heterocyclyl" or "cycloheteroalkyl" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S, or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —N(alkyl)$_3^+$, —$NR_aSO_2$, —$NR_aSO_2R_c$, —$SO_2R_c$—$SO_2NR_aR_b$, —$SO_2NR_aC$(=O) $R_b$, $SO_3H$, —$PO(OH)_2$, —C(=O)$R_a$, —$CO_2R_a$, —C(=O) $NR_aR_b$, —C(=O)(C$_{1-4}$alkylene)$NR_aR_b$, —C(=O)$NR_a$ (SO$_2$)$R_b$, —$CO_2$(C$_{1-4}$alkylene)$NR_aR_b$, —$NR_aC$(=O)$R_b$, —$NR_aCO_2R_b$, —$NR_a$(C$_{1-4}$alkylene)$CO_2R_b$, =N—OH, =N—O-alkyl, aryl, cycloalkyl, heterocyclo, and/or heteroaryl, wherein $R_a$, $R_b$, and $R_c$ are as defined above for substituted alkyl groups, and are also in turn optionally substituted as recited above. When a heterocyclo is substituted with a further ring, said ring in turn is optionally substituted with one to two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$ alkyl), —S(C$_{1-4}$alkyl), —NH$_2$, NH(C$_{1-4}$alkyl), N(C$_{1-4}$ alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), and/or C(=O) (C$_{1-4}$alkylene)N(C$_{1-4}$alkyl)$_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like. Exemplary bicyclic heterocyclo groups include quinuclidinyl.

Preferred heterocyclo groups in compounds of formula (I) include

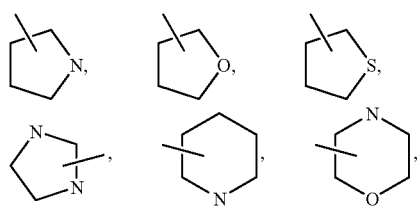

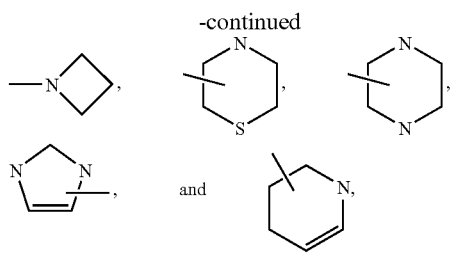

which optionally may be substituted.

The term "heteroaryl" alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated, and may include aryl, cycloalkyl, heteroaryl or cycloheteroalkyl groups. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents which may be any of the substituents set out for alkyl and can be selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —N(alkyl)$_3^+$, —$NR_aSO_2$, —$NR_aSO_2R_c$, —$SO_2R_c$—$SO_2NR_aR_b$, —$SO_2NR_aC$(=O) $R_b$, $SO_3H$, —$PO(OH)_2$, —C(=O)$R_a$, —$CO_2R_a$, —C(=O) $NR_aR_b$, —C(=O)(C$_{1-4}$alkylene)$NR_aR_b$, —C(=O)$NR_a$ (SO$_2$)$R_b$, —$CO_2$(C$_{1-4}$alkylene)$NR_aR_b$, —$NR_aC$(=O)$R_b$, —$NR_aCO_2R_b$, —$NR_a$(C$_{1-4}$alkylene)$CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of (C$_{1-4}$)alkyl, (C$_{2-4}$)alkenyl, halogen, hydroxy, cyano, nitro, CF$_3$, O(C$_{1-4}$ alkyl), OCF$_3$, C(=O)H, C(=O)(C$_{1-4}$alkyl), CO$_2$H, CO$_2$ (C$_{1-4}$ alkyl), NHCO$_2$(C$_{1-4}$alkyl), —S(C$_{1-4}$alkyl), —NH$_2$, NH(C$_{1-4}$ alkyl), N(C$_{1-4}$alkyl)$_2$, N(C$_{1-4}$alkyl)$_3^+$, SO$_2$(C$_{1-4}$ alkyl), C(=O)(C$_{1-4}$alkylene)NH$_2$, C(=O)(C$_{1-4}$alkylene)NH (alkyl), and/or C(=O)(C$_{1-4}$alkylene)N(C$_{1-4}$alkyl)$_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

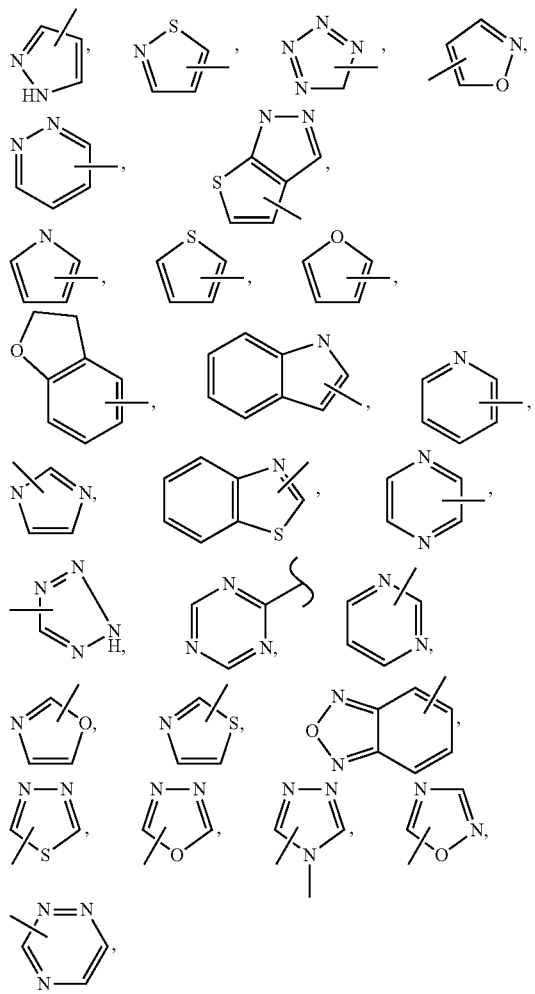

and the like.

The term "heterocyclylalkyl" or "heterocycloalkyl" or "cycloheteroalkylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an —OH group.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g. imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

The terms pharmaceutically acceptable "salt" and "salts" may refer to basic salts formed with inorganic and organic bases. Such salts include ammonium salts; alkali metal salts, such as lithium, sodium, and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine, and the like; and zwitterions, the so-called "inner salts." Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid, or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric, or citric acid, such as amino acids, (for example aspartic or glutamic acid or lysine or arginine), or benzoic acid, or with organic sulfonic acids, such as ($C_1$-$C_4$) alkyl or arylsulfonic acids, which are unsubstituted or substituted, for example by halogen, for example methanesulfonic acid or p-toluenesulfonic acid.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

Any compound that can be converted in vivo to provide the bioactive agent (i.e., the compound of formula I) is a prodrug within the scope and spirit of the invention.

The term "prodrug" denotes a compound which, upon administration to a subject, undergoes chemical conversion by metabolic or chemical processes to yield a compound of the formula, and/or a salt and/or solvate thereof. For example, compounds containing a carboxy group can form physiologically hydrolyzable esters which serve as prodrugs by being hydrolyzed in the body to yield formula compounds per se. Such prodrugs are preferably administered orally since hydrolysis in many instances occurs principally under the influence of the digestive enzymes. Parenteral administration may be used where the ester per se is active, or in those instances where hydrolysis occurs in the blood.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds. Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl, or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl, and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

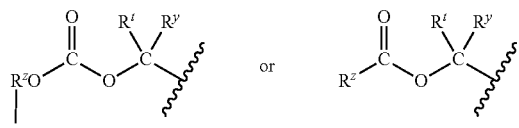

wherein $R^z$, $R^t$, and $R^y$ are H, alkyl, aryl, or arylalkyl; however, $R^zO$ cannot be HO.

Examples of such prodrug esters include

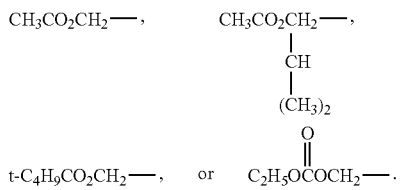

Other examples of suitable prodrug esters include

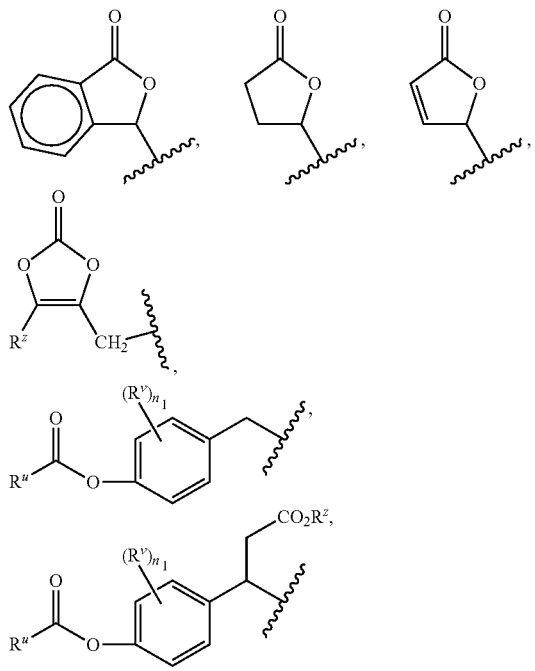

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl, or alkoxyl, and $n_1$ is 0, 1, or 2.

The term "tautomer" refers to compounds of the formula I and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to treat or prevent diabetes and/or obesity.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

Synthesis

Compounds of formulae I and Ia may be prepared as shown in the following reaction schemes and the description thereof, as well as relevant literature procedures that may be used by one skilled in the art. Exemplary reagents and procedures for these reactions appear hereinafter and in the working Examples.

SCHEME 1

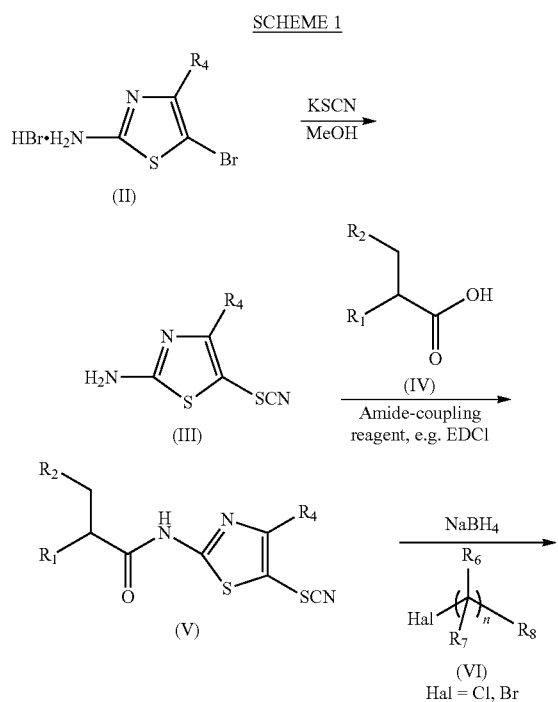

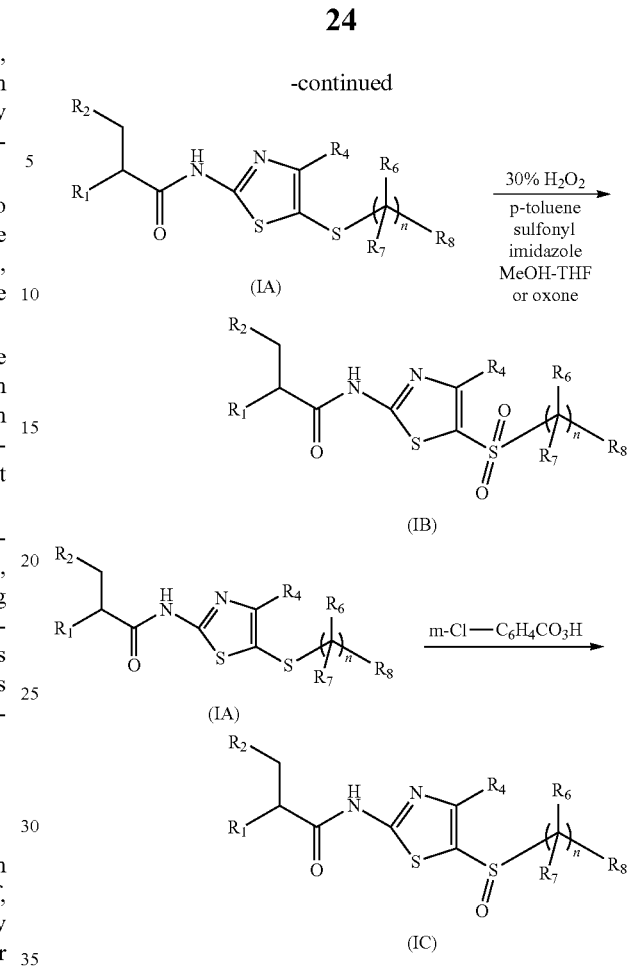

Scheme 1 describes a method for preparing compounds of formulae IA, IB, and IC (subsets of compounds of formula I). The 5-thiocyanatothiazol-2-amine III can be obtained by the treatment of commercially available 2-amino-5-bromothiazole hydrobromide II with potassium thiocyanate. The amide V can be obtained from the reaction of amine III with an acid IV, for instance by following the procedure from WO 02/46173, using appropriate amide coupling reagents, such as DEPBT, BOP, EDAC/HOBT, EDAC/HOAT, or PyBOP, or those reagents described in "The Practice of Peptide Synthesis" (Spring-Verlag, $2^{nd}$ Ed., Bodanszky, Miklos, 1993). Reduction of the intermediate thiocyanate V with sodium borohydride followed by treatment of a chloride or bromide VI, which can be obtained commercially or are readily prepared by methods known in the literature or other methods used by one skilled in the art, provides the corresponding sulfides, which are compounds of formula IA (subsets of compounds of formula I). Subsequent oxidation of compounds IA with an appropriate oxidizing reagent such as $H_2O_2$/p-toluenesulfonyl imidazole, or oxone, or other reagents used by one skilled in the art provides the corresponding sulfones, which are compounds of formula IB (subsets of compounds of formula I). Additionally, oxidation of compounds IA with an appropriate oxidizing agent such as meta-chloroperbenzoic acid, or other agents used by one skilled in the art provides the corresponding sulfoxides, which are compounds of formula IC (subsets of compounds of formula I).

SCHEME 2

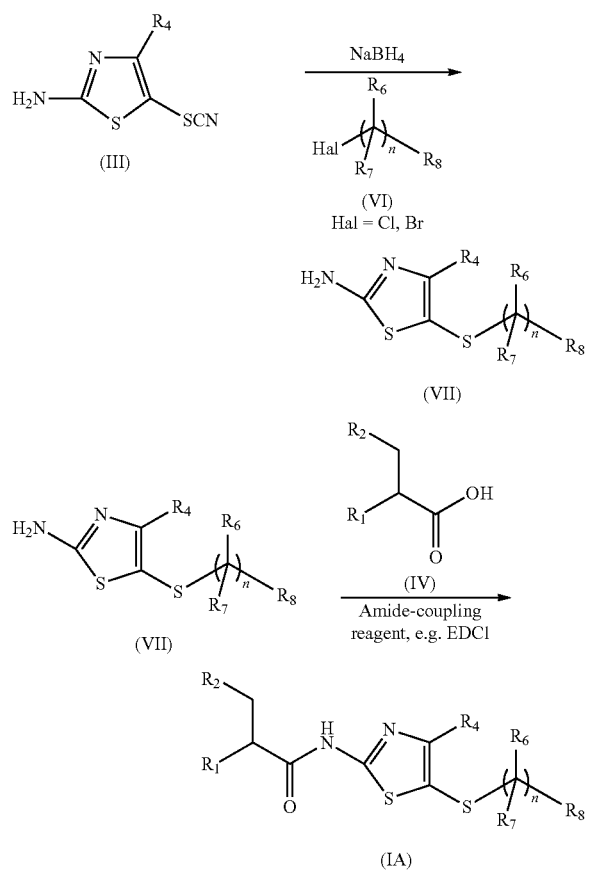

Scheme 2 describes an alternative method for preparing compounds of formula IA (subsets of compounds of formula I). Reduction of the intermediate thiocyanate III with sodium borohydride followed by treatment of a chloride or bromide VI, which can be obtained commercially or prepared by methods known in the literature or other methods used by one skilled in the art, provides an intermediate thioalkyl thiazole VII. Amide IA can be obtained from the reaction of amine VII with an acid IV, for instance by following the procedure from WO 02/46173, using appropriate amide coupling reagents, such as DEPBT, BOP, EDAC/HOBT, EDAC/HOAT, PyBOP, or those reagents described in "The Practice of Peptide Synthesis" (Spring-Verlag, 2$^{nd}$ Ed., Bodanszky, Miklos, 1993), to yield compounds of formula IA (subsets of compounds of formula I).

SCHEME 3

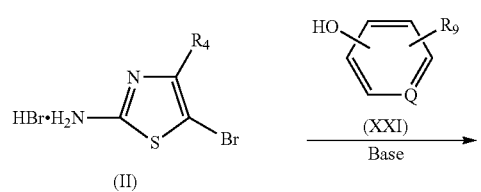

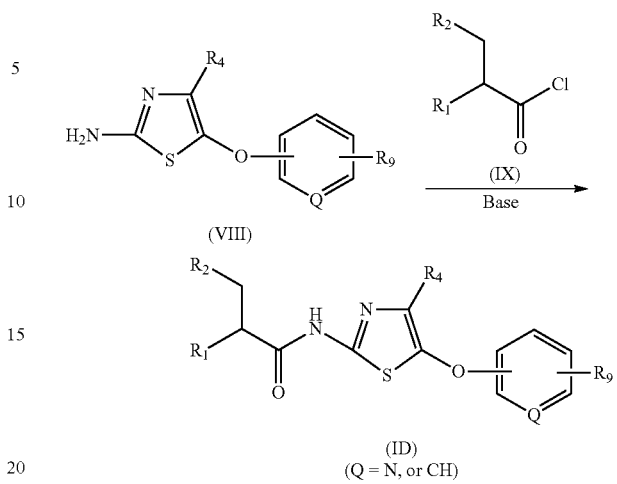

Q = N, CH
R$_9$ = CO$_2$H, tetrazole, alkyl, alkoxy, halogen, amino, CN, CO$_2$R$^a$, or CONR$^a$R$^b$ where R$^a$ and R$^b$ are the same or different and are H or alkyl)

Scheme 3 describes a method for preparing compounds of formula ID (subsets of compounds of formula I). An aminothiazole intermediate VIII can be obtained by treatment of commercially available 2-amino-5-bromothiazole monohydrobromide II with the appropriately substituted hydroxybenzenes or hydroxyheteroarenes XXI, which can be obtained commercially or prepared by methods known in the literature or other methods used by one skilled in the art, in the presence of a base (for instance cesium carbonate in acetone at reflux; procedure from WO 02/50071). The desired amide ID can be obtained from reaction of the amine VIII with an acid chloride IX (prepared by treatment of the corresponding acid IV with oxalyl chloride/DMF) using appropriate reagents, such as pyridine, pyridine/DMAP, or NaHCO$_3$, to yield compounds of formula ID (subsets of compounds of formula I). Alternatively, amide ID can be obtained from the reaction of aminve VIII with the corresponding carboxylic acid IV using appropriate amide coupling reagents, such as BOP, EDAC/HOBT or EDAC/HOAT, PyBOP, etc.

SCHEME 4

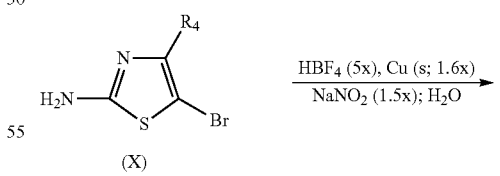

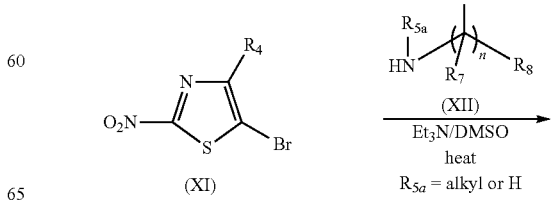

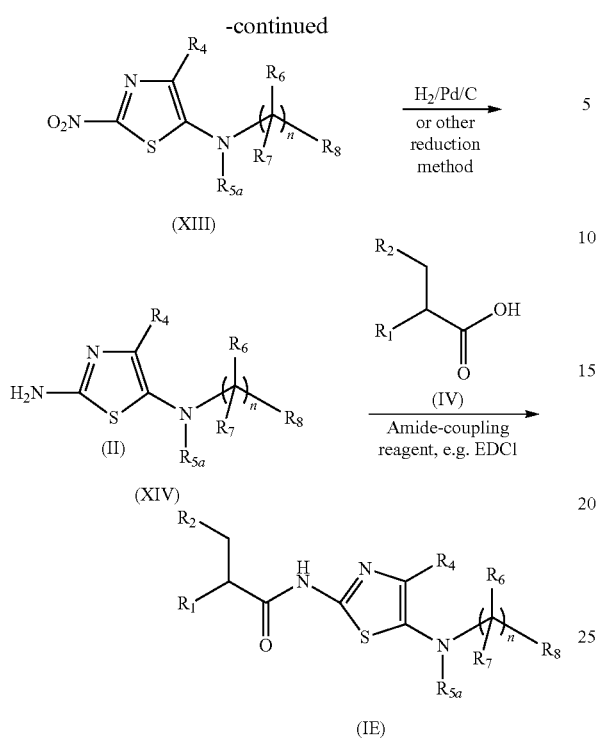

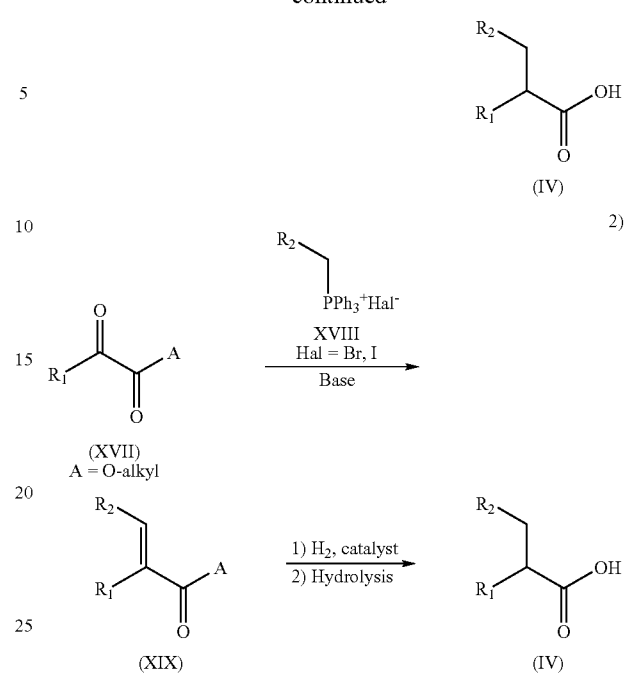

Scheme 4 describes a method for preparing compounds of formula IE (a subset of compounds of formula I). The 2-amino-5-bromothiazole X can be converted to the corresponding 2-nitro-5-bromothiazole XI (for instance, under typical Sandmeyer type conditions, e.g., *Bioorg. Med. Chem. Lett.* 2004, 14:5521-5525). The bromothiazole XI can then be reacted with a variety of amines XII (including primary amines, where $R_{5a}$=H, and secondary amines, where $R_{5a}$=alkyl) in a displacement reaction to provide 5-amino-2-nitro-thiazoles XIII. The nitrothiazoles XIII can be reduced to the corresponding aminothiazoles XIV by a variety of methods, for instance hydrogenation or with sodium dithionite. The desired amide IE can then be obtained from the reaction of the aminothiazoles XIV with a carboxylic acid IV, for instance by following the procedure from WO 2002/46173, using appropriate amide coupling reagents, such as DEPBT, BOP, EDAC/HOBT, EDAC/HOAT, PyBOP, or those reagents described in "The Practice of Peptide Synthesis" (Spring-Verlag, 2$^{nd}$ Ed., Bodanszky, Miklos, 1993). Alternatively, amide IE can be obtained from the reaction of aminothiazoles XIV with the corresponding acid chlorides IX obtained from acids IV (via, e.g., oxalyl chloride).

Carboxylic acids IV can be prepared through either of the two routes shown in Scheme 5. In route 1, acids IV are prepared via a 2-step procedure involving: 1) alkylation of a carboxylic acid derivative XV with an alkyl halide XVI in the presence of a base (e.g. LiN(TMS)$_2$ or LiN(iPr)$_2$, etc.), for instance, as described in WO 2002/46173 and WO 2004/52869) and 2) hydrolysis of the alkylated carboxylic acid derivative under either basic or acidic conditions. It should be noted if A is a chiral moiety [for instance, pseudoephedrine (A. Myers et al., *J. Am. Chem. Soc.*, 1994, 116:9361 and 1997, 119:6496) or chiral oxazolidinones (*J. Am. Chem. Soc.*, 1982, 104:1737)], then the individual enantiomers of carboxylic acid IV can be readily obtained from the alkylation reaction. In route 2, the α-ketoester XVII is reacted with an appropriate Wittig reagent XVIII (prepared from the reaction of alkyl halide XVI with triphenylphosphine) to give the α,β unsaturated ester XIX. Hydrogenation of XIX, followed by ester hydrolysis, provides acids IV. It should be noted that if the hydrogenation of XIX is carried out with an appropriate chiral catalyst (for instance, as described in WO 2006/016178), then the individual enantiomers of carboxylic acid IV can be readily obtained.

SCHEME 5

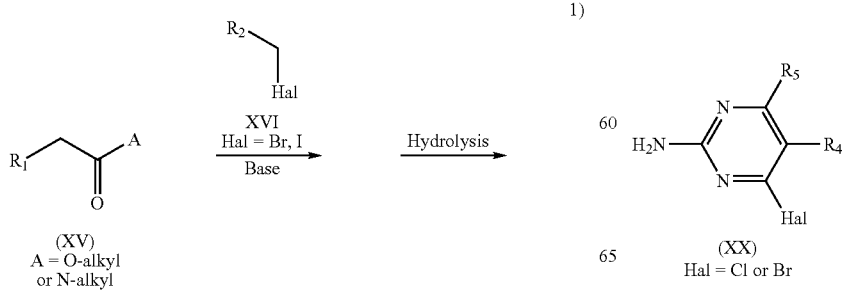

SCHEME 6

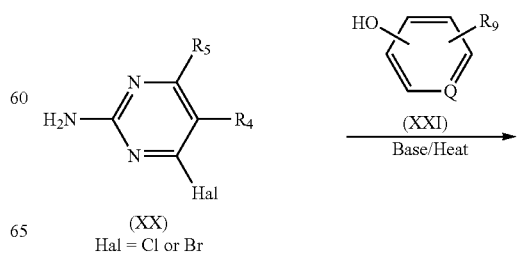

-continued

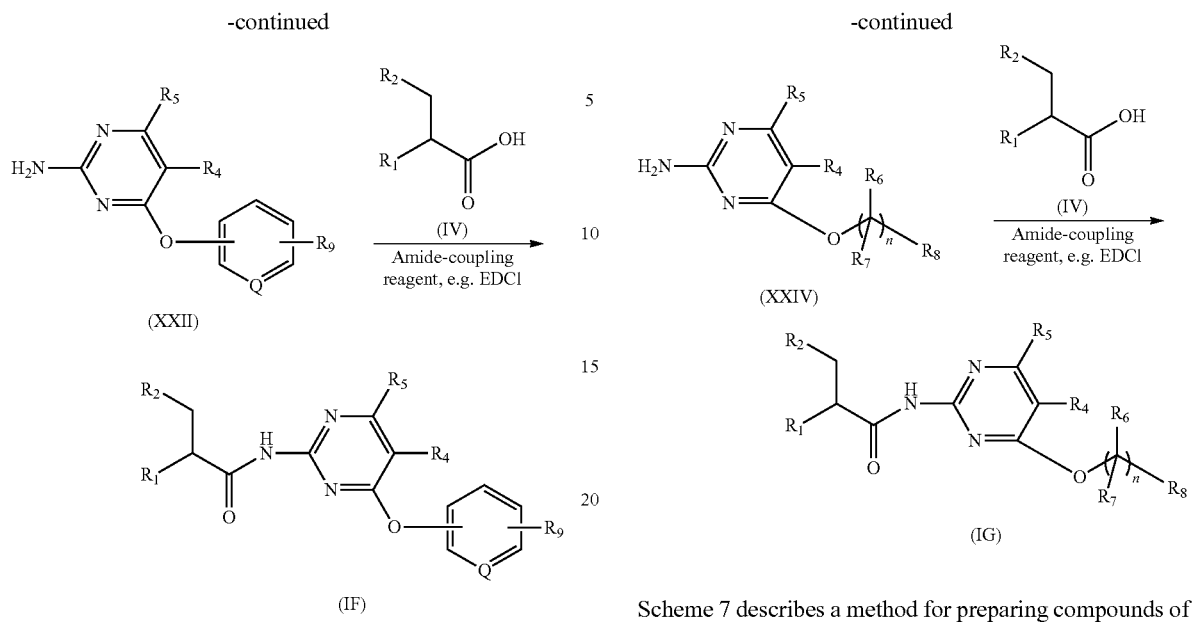

(XXII)

(IF)

Q = N, CH
$R_9$ = $CO_2H$, tetrazole, alkyl, alkoxy, halogen, amino, CN, $CO_2R^a$, or $CONR^aR^b$ where $R^a$ and $R^b$ are the same or different and are H or alkyl)

Scheme 6 describes a method for preparing compounds of formula IF (a subset of compounds of formula I). An aminopyrimidine intermediate XXII can be obtained by treatment of 2-amino-halopyrimidine XX with an appropriately substituted hydroxybenzene or hydroxyheteroarenes (XXI) which can be obtained commercially or prepared by methods known in the literature or other methods used by one skilled in the art, in the presence of a base (for instance cesium carbonate in DMF with heating; procedure as described in *Bioorg. Med. Chem. Lett.*, 2001, 11:2185-2188). The desired amide IF can be obtained from reaction of the aminopyrimidine XXII with an acid IV, for instance by following the procedure from WO 2002/46173, using appropriate amide coupling reagents, such as DEPBT, BOP, EDAC/HOBT, EDAC/HOAT, PyBOP, or those reagents described in "The Practice of Peptide Synthesis" (Spring-Verlag, $2^{nd}$ Ed., Bodanszky, Miklos, 1993). Alternatively, amide IF can be obtained from the reaction of aminopyrimidine XXII with the corresponding acid chlorides IX obtained from acids IV (via reaction with, e.g., oxalyl chloride).

SCHEME 7

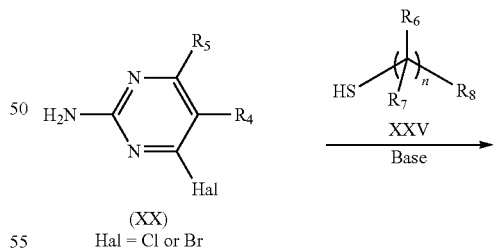

(XX)
Hal = Cl or Br

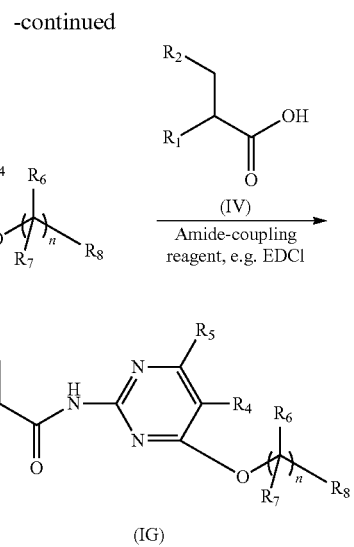

(XXIV)

(IG)

Scheme 7 describes a method for preparing compounds of formula IG (a subset of compounds of formula I). An aminopyrimidine intermediate XXIV can be obtained by treatment of an 2-amino-halopyrimidine XX with the alkoxide of an appropriately substituted alcohol (XXIII) (the alkoxide can be prepared from the reaction of the alcohol with an appropriate base, e.g. sodium hexamethyldisilazide) with heating; as generally described in *J. Chem. Res.*, 2005, 747-749. The desired amide IG can be obtained from reaction of the aminopyrimidine XXIV with an acid IV, for instance by following the procedure from WO 2002/46173, using appropriate amide coupling reagents, such as DEPBT, BOP, EDAC/HOBT, EDAC/HOAT, or PyBOP and the like as described for Scheme 6. Alternatively, amide IG can be obtained from the reaction of aminopyrimidine XXIV with the corresponding acid chlorides IX obtained from acids IV (via reaction with, e.g., oxalyl chloride).

SCHEME 8

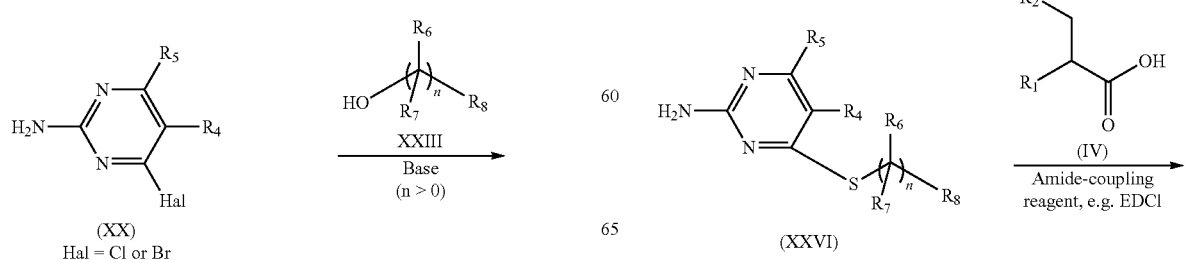

(XX)
Hal = Cl or Br (XXVI)

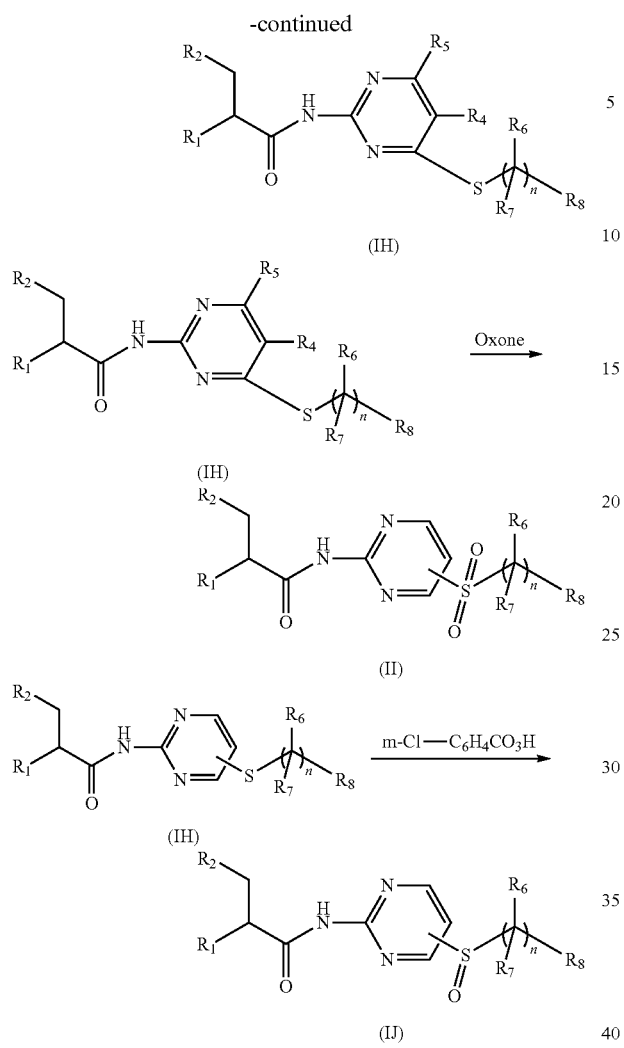

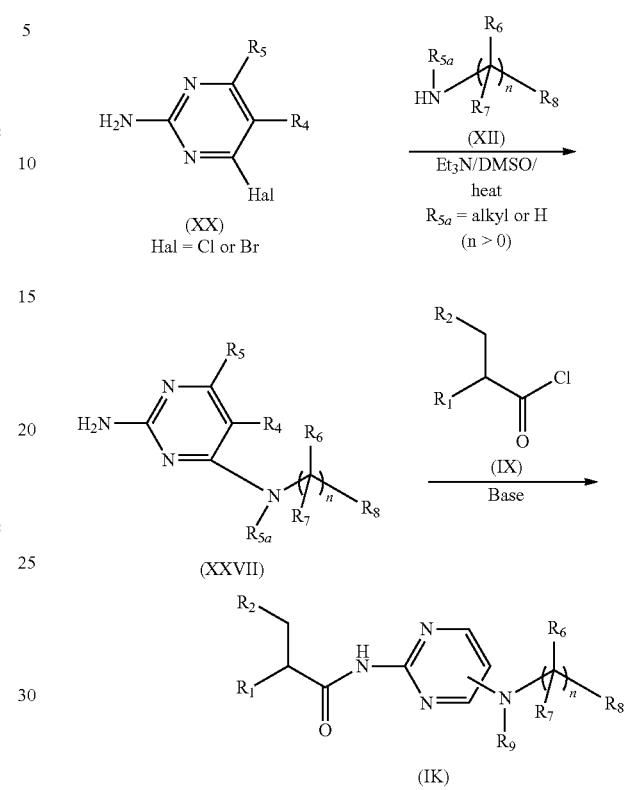

Scheme 8 describes a method for preparing compounds of formulae IH, II, and IJ (subsets of compounds of formula I). An aminopyrimidine intermediate XXVI can be obtained by treatment of an 2-amino-halopyrimidine XX with a thiolate (generated from a substituted thiol XXV using an appropriate base such as NaH or NaN(TMS)$_2$). The amide IH can be obtained from the reaction of amine XXVI with an acid IV, for instance by following the procedure from WO 02/46173, using appropriate amide coupling reagents, such as DEPBT, BOP, EDAC/HOBT, EDAC/HOAT, or PyBOP, or those reagents described in "The Practice of Peptide Synthesis" (Spring-Verlag, 2$^{nd}$ Ed., Bodanszky, Miklos, 1993). Alternatively, amide IH can be obtained from the reaction of amine XXVI with the corresponding acid chlorides IX obtained from acids IV (via reaction with, e.g., oxalyl chloride). Subsequent oxidation of sulfide-containing compounds IH with an appropriate oxidizing reagent such as oxone, or other reagents used by one skilled in the art provides the corresponding sulfones, which are compounds of formula II (subsets of compounds of formula I). Additionally, oxidation of compounds IH with an appropriate oxidizing agent such as meta-chloroperbenzoic acid, or other agents used by one skilled in the art provides the corresponding sulfoxides, which are compounds of formula IJ (subsets of compounds of formula I).

Scheme 9 describes a method for preparing compounds of formula IK (a subset of compounds of formula I). An aminopyrimidine intermediate XXVII can be obtained by treatment of an 2-amino-halopyrimidine XX with a primary or secondary amine with heating in the presence of a tertiary amine (for example, as in *J. Am. Chem. Soc.,* 2002, 124:1594-1596). The desired amide IK can be obtained from reaction of the aminopyrimidine XXVII with an acid chloride IX (prepared by treatment of the corresponding acid IV with oxalyl chloride/DMF) in the presence of an appropriate base. Alternatively, amide IK can be obtained from the reaction of aminopyrimidine XXVII with the corresponding carboxylic acid IV using appropriate amide coupling reagents, such as BOP, EDAC/HOBT, EDAC/HOAT, or PyBOP, as described for Scheme 6.

SCHEME 10

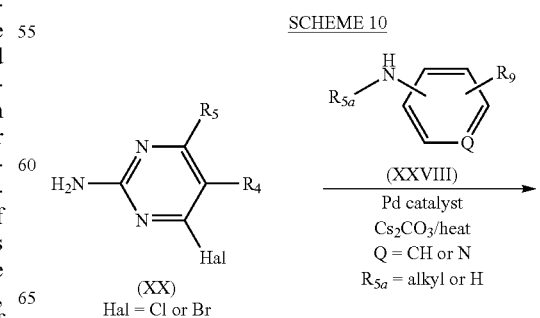

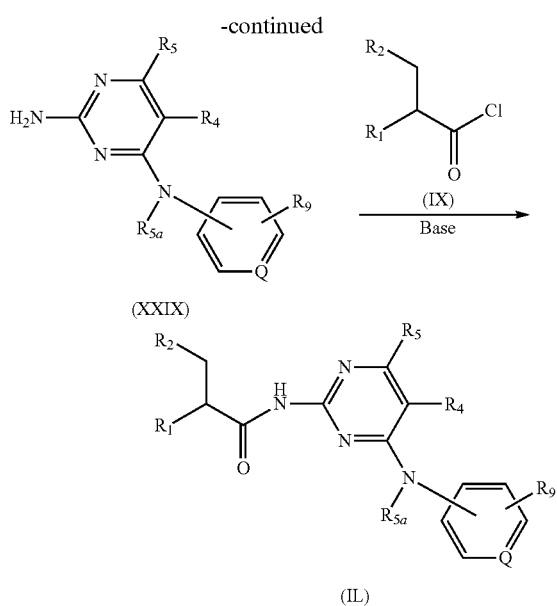

Scheme 10 describes a method for preparing compounds of formula IL (a subset of compounds of formula I). An aminopyrimidine intermediate XXIX can be obtained by treatment of 2-amino-halopyrimidine XX with an appropriately substituted aniline or aminoheteroarenes (XXVIII) which can be obtained commercially or prepared by methods known in the literature or other methods used by one skilled in the art, in the presence of a base and a palladium catalyst with an appropriate ligand (for instance cesium carbonate and $Pd_2(dba)_3$/DPPF with heating; procedure as described in *J. Med. Chem.*, 2005, 48:4892-4909). The desired amide IL can be obtained from reaction of the aminopyrimidine XXIX with an acid chloride IX obtained from acids IV (via reaction with, e.g., oxalyl chloride) in the presence of a base. Alternatively, amide IL can be obtained from reaction of aminopyrimidine XXIX with an acid IV by following the procedure from WO 2002/46173, using appropriate amide coupling reagents, such as DEPBT, BOP, EDAC/HOBT, EDAC/HOAT, or PyBOP, or those reagents described in "The Practice of Peptide Synthesis" (Spring-Verlag, 2$^{nd}$ Ed., Bodanszky, Miklos, 1993).

It will be appreciated in Schemes 1 to 10 any of the ring systems

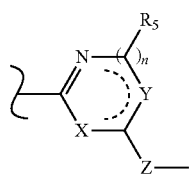

as defined above may be employed in place of the thiazole ring system and pyrimidine ring system to produce corresponding compounds I of the invention.

Utilities and Combinations

A. Utilities

The compounds of the present invention possess activity as enhancers of activity of the enzyme glucokinase, and, therefore, may be used in the treatment of diseases associated with glucokinase activity.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

Metabolic Syndrome or "Syndrome X" is described in Ford, et al., *J. Am. Med. Assoc.* 2002, 287:356-359 and Arbeeny, et al., *Curr. Med. Chem.—Imm., Endoc. & Metab. Agents* 2001, 1:1-24.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other enhancers of activity of glucokinase or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-infective agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-ischemic agents, anti-cancer agents, anti-cytotoxic agents, anti-restenotic agents, anti-pancreatic agents, lipid lowering agents, appetite suppressants, memory enhancing agents, and cognitive agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones (PPARgamma agonists): ciglitazone, pioglitazone, troglitazone, rosiglitazone; non-thiazolidinedione PPAR-gamma agonists; selective PPARgamma modulators (SPPARMs; e.g. metaglidasen from Metabolex); PPAR-alpha agonists; PPAR alpha/gamma dual agonists; PPAR delta agonists, PPARalpha/gamma/delta pan agonists; SGLT2 inhibitors; dipeptidyl peptidase-IV (DPP4) inhibitors; aldose reductase inhibitors; RXR agonists: JTT-501, MX-6054, DRF2593, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's farglitazar (GI-262570), englitazone (CP-68722, Pfizer), or darglitazone (CP-86325, Pfizer), isaglitazone (MIT/J&J), JTT-501 (JPNT/P&U), L-895645 (Merck), R-1 19702 (Sankyo/WL), NN-2344 or balaglitazone (Dr. Reddy/NN), or YM-440 (Yamanouchi).

Suitable PPAR alpha/gamma dual agonists include muraglitazar (Bristol-Myers Squibb), tesaglitazar (Astra/Zeneca), naveglitazar (Lilly/Ligand); AVE-0847 (Sanofi-Aventis); TAK-654 (Takeda), as well as those disclosed by Murakami et al, "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", Diabetes 47:1841-1847 (1998), WO 01/21602 and U.S. Pat. No. 6,414,002, the disclosure of which is incorporated herein by reference, employing dosages as set out therein, which compounds designated as preferred are preferred for use herein. Suitable PPARdelta agonists include, for example, GW-501516 (Glaxo). Suitable PPARalpha/gamma/delta pan agonists include, for example, GW-677954 (Glaxo).

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptin (Bristol-Myers Squibb), vildagliptin (Novartis) and sitagliptin (Merck) as well as those disclosed in WO 99/38501, WO 99/46272, WO 99/67279 (PROBIODRUG), WO 99/67278 (PROBIODRUG), WO 99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al., Biochemistry, 38(36): 11597-11603 (1999), TSL-225 (tryptophyl-1,2,3,4-tetrahydroisoquinoline-3-carboxylic acid) as disclosed by Yamada et al., Bioorg. & Med. Chem. Lett., 8:1537-1540 (1998), 2-cyanopyrrolidides and 4-cyanopyrrolidides, as disclosed by Ashworth et al, Bioorg. & Med. Chem. Lett., Vol. 6, No. 22, pp. 1163-1166 and 2745-2748 (1996), employing dosages as set out in the above references.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) include GLP-1(1-36) amide, GLP-1(7-36) amide, GLP-1(7-37) (as disclosed in U.S. Pat. No. 5,614,492 to Habener), as well as AC2993 (Amylin), and LY-315902 (Lilly).

Other anti-diabetic agents that can be used in combination with compounds of the invention include ergoset and D-chiroinositol.

Suitable anti-ischemic agents include, but are not limited to, those described in the Physician's Desk Reference and NHE inhibitors, including those disclosed in WO 99/43663.

Examples of suitable anti-infective agents are antibiotic agents, including, but not limited to, those described in the Physicians' Desk Reference.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., torcetrapib (Pfizer)), and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983, and 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440; and related statin compounds disclosed in U.S. Pat. No. 5,753,675; pyrazole analogs of mevalonolactone derivatives, as disclosed in U.S. Pat. No. 4,613,610; indene analogs of mevalonolactone derivatives, as disclosed in PCT application WO 86/03488; 6-[2-(substituted-pyrrol-1-yl)alkyl)pyran-2-ones and derivatives thereof, as disclosed in U.S. Pat. No. 4,647,576; Searle's SC-45355 (a 3-substituted pentanedioic acid derivative) dichloroacetate; imidazole analogs of mevalonolactone, as disclosed in PCT application WO 86/07054; 3-carboxy-2-hydroxy-propane-phosphonic acid derivatives, as disclosed in French Patent No. 2,596,393; 2,3-disubstituted pyrrole, furan and thiophene derivatives, as disclosed in European Patent Application No. 0221025; naphthyl analogs of mevalonolactone, as disclosed in U.S. Pat. No. 4,686,237; octahydronaphthalenes, such as disclosed in U.S. Pat. No. 4,499,289; keto analogs of mevinolin (lovastatin), as disclosed in European Patent Application No.0142146 A2; and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin, and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem. (1988), Vol. 31, No. 10, pp. 1869-1871, including isoprenoid(phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2:1-40 (1996).

In addition, other squalene synthetase inhibitors suitable for use herein include the terpenoid pyrophosphates disclosed by P. Ortiz de Montellano et al, J. Med. Chem. (1977), 20:243-249, the farnesyl diphosphate analog A and presqualene pyrophosphate (PSQ-PP) analogs as disclosed by Corey and Volante, J. Am. Chem. Soc. (1976), 98:1291-1293, phosphinylphosphonates reported by McClard, R. W. et al., J.A.C.S. (1987), 109:5544 and cyclopropanes reported by Capson, T. L., Ph.D. dissertation, June, 1987, Dept. Med. Chem. U of Utah, Abstract, Table of Contents, pp. 16, 17, 40-43, 48-51, Summary.

The fibric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future, 24:9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1):77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), pp. 173-98, Publisher: CRC, Boca Raton, Fla.; "ACAT inhibitors: potential anti-atherosclerotic agents", Sliskovic et al, Curr. Med. Chem. (1994), 1(3):204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6):359-62, or TS-962 (Taisho Pharmaceutical Co. Ltd.).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitors for use in combination with the compounds of the invention include SCH48461 (Schering-Plough), as well as those disclosed in Atherosclerosis, 115:45-63 (1995) and J. Med. Chem., 41:973 (1998).

Examples of suitable ileal $Na^+$/bile acid cotransporter inhibitors for use in combination with the compounds of the invention include compounds as disclosed in Drugs of the Future, 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", Brit. J. Pharmacology (1997), 120:1199-1206, and Cornicelli et al., "15-Lipoxygenase and its Inhibition: A Novel Therapeutic Target for Vascular Disease", Current Pharmaceutical Design (1999), 5: 11-20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, and those discussed in D. L. Hertzog, Expert Opin. Ther. Patents (2004), 14:1435-1452.

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983, and 5,488,064, with AJ9677, L750,355, and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson), or axokine (Regeneron), with sibutramine and topiramate being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., HP-228); leptin or mimentics; 11-beta-hydroxysteroid dehydrogenase type-I inhibitors; urocortin mimetics, CRF antagonists, and CRF binding proteins (e.g., RU-486, urocortin).

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; famesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators; and monoclonal antibodies. Additional anti-cancer agents are disclosed in EP 1177791. The compounds of the invention may also be used in conjunction with radiation therapy.

Examples of suitable memory enhancing agents, anti-dementia agents, or cognitive agents for use in combination with the compounds of the present invention include, but are not limited to, donepezil, rivastigmine, galantamine, memantine, tacrine, metrifonate, muscarine, xanomelline, deprenyl, and physostigmine.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules, or powders; sublingually; bucally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules, or powders. The dose for adults is between 0.25 and 2,000 mg per day, preferably between 1 and 500 mg, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

Abbreviations

The following abbreviations are employed in the Examples and elsewhere herein:
Ph=phenyl
Bn=benzyl
t-Bu=tertiary butyl
i-Bu=iso-butyl
Me=methyl
Et=ethyl
Pr=propyl
iPr=isopropyl
Bu=butyl
AIBN=2,2'-Azobisisobutyronitrile
TMS=trimethylsilyl
TMSCHN$_2$=(trimethylsilyl)diazomethane
TMSN$_3$=trimethylsilyl azide
TBS=tert-butyldimethylsilyl
FMOC=fluorenylmethoxycarbonyl
Boc or BOC=tert-butoxycarbonyl
Cbz=carbobenzyloxy or carbobenzoxy or benzyloxycarbonyl
THF=tetrahydrofuran
Et$_2$O=diethyl ether
hex=hexanes
EtOAc=ethyl acetate
DMF=dimethyl formamide
MeOH=methanol
EtOH=ethanol
DCM=dichloromethane
i-PrOH=isopropanol DMSO=dimethyl sulfoxide
DME=1,2 dimethoxyethane
DMA=N,N-dimethylacetylamide
DCE=1,2 dichloroethane
HMPA=hexamethyl phosphoric triamide
HOAc or AcOH=acetic acid
TFA=trifluoroacetic acid
DIEA or DIPEA or i-$Pr_2$NEt or Hunig's Base=diisopropylethylamine
TEA or $Et_3$N=triethylamine
NMM=N-methyl morpholine
NBS=N-bromosuccinimide
NCS=N-chlorosuccinimide
DMAP=4-dimethylaminopyridine
DEPBT=3-diethoxyphosphoryloxy-1,2,3-benzotriazin-4[3H]-one
mCPBA=3-chloroperoxybenzoic acid
$NaBH_4$=sodium borohydride
$NaBH(OAc)_3$=sodium triacetoxyborohydride
$NaN_3$=sodium azide
DIBALH=diisobutyl aluminum hydride
$LiAlH_4$=lithium aluminum hydride
n-BuLi=n-butyllithium
Oxone®=monopersulfate
Pd/C=palladium on carbon
$PXPd_2$=Dichloro(chlorodi-tert-butylphosphine)palladium (II) dimer or $[PdCl_2(t-Bu)_2PCl]_2$
$PtO_2$=platinum oxide
KOH=potassium hydroxide
NaOH=sodium hydroxide
LiOH=lithium hydroxide
LiOH.$H_2$O=lithium hydroxide monohydrate
HCl=hydrochloric acid
$H_2SO_4$=sulfuric acid
$H_2O_2$=hydrogen peroxide
$Al_2O_3$=aluminum oxide
$K_2CO_3$=potassium carbonate
$Cs_2CO_3$=cesium carbonate
$NaHCO_3$=sodium bicarbonate
$ZnBr_2$=zinc bromide
$MgSO_4$=magnesium sulfate
$Na_2SO_4$=sodium sulfate
KSCN=potassium thiocyanate
$NH_4$Cl=Ammonium chloride
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2$O=1-hydroxybenzotriazole hydrate
HOAT=1-Hydroxy-7-azabenzotriazole
PyBOP reagent or BOP reagent=benzotriazol-1-yloxy-tris(dimethylamino)phosphonium hexafluorophosphate
NaN$(TMS)_2$=sodium hexamethyldisilazide or sodium bis(trimethylsilyl)amide
$Ph_3$P=triphenylphosphine
Pd$(OAc)_2$=Palladium acetate
$(Ph_3P)_4Pd°$=tetrakis triphenylphosphine palladium
$Pd_2(dba)_3$=tris(dibenzylacetone)dipalladium
DPPF=1,1'-Bis(diphenylphosphino)ferrocene
HATU=2-(7-aza-1H-benzotriazole-1-yl)-1,1,3,3-tetramethyluronium hexafluorophosphate, 2-(3H-[1,2,3]triazolo[4,5-b]pyridin-3-yl)-1,1,3,3-tetramethylisouronium hexafluorophosphate(V)
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
$H_2$=hydrogen
Ar=argon
$N_2$=nitrogen
Equiv=equivalent(s)
min=minute(s)
h or hr=hour(s)
L=liter
mL=milliliter
μL=microliter
g=gram(s)
mg=milligram(s)
mol=moles
mmol=millimole(s)
meq=milliequivalent
RT or R.T.=room temperature
AT=ambient temperature
sat or sat'd=saturated
aq.=aqueous
TLC=thin layer chromatography
HPLC=high performance liquid chromatography
HPLC $R_t$=HPLC retention time
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet mp=melting point

EXAMPLES

The following working Examples serve to better illustrate, but not limit, some of the preferred embodiments of the present invention.

General

The term HPLC refers to a Shimadzu high performance liquid chromatography with one of following methods:

Method A: YMC or Phenomenex C18 5 micron 4.6×50 mm column using a 4 minute gradient of 0-100% solvent B [90% MeOH: 10% $H_2$O:0.2% $H_3PO_4$] and 100-0% solvent A [10% MeOH:90% $H_2$O:0.2% $H_3PO_4$] with 4 mL/min flow rate and a 1 min. hold, an ultra violet (uv) detector set at 220 nm.

Method B: Phenomenex S5 ODS 4.6×30 mm column, gradient elution 0-100% B/A over 2 min (solvent A=10% MeOH/$H_2$O containing 0.1% TFA, solvent B=90% MeOH/$H_2$O containing 0.1% TFA), flow rate 5 mL/min, UV detection at 220 nm.

Method C: YMC S7 ODS 3.0×50 mm column, gradient elution 0-100% B/A over 2 min (solvent A=10% MeOH/$H_2$O containing 0.1% TFA, solvent B=90% MeOH/$H_2$O containing 0.1% TFA), flow rate 5 mL/min, UV detection at 220 nm.

The term prep HPLC refers to an automated Shimadzu HPLC system using a mixture of solvent A (10% MeOH/90%$H_2$O/0.2%TFA) and solvent B (90% MeOH/10%$H_2$O/0.2% TFA). The preparative columns are packed with YMC or Phenomenex ODS C18 5 micron resin or equivalent.

The following Examples are illustrative of preferred compounds of the invention.

Example 1

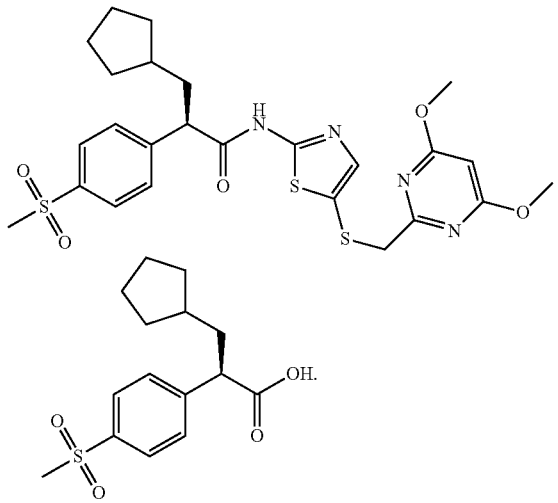

Note: The following procedure was adapted from WO 02/46173.

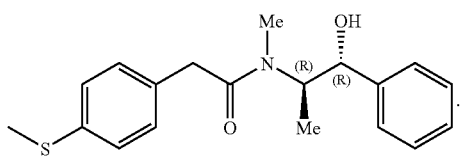

i

To a solution of 4-methythio-phenylacetic acid (5.4 g, 29.6 mmol) and K$_2$CO$_3$ (12.3 g, 88.8 mmol) in acetone (40 mL) was added dropwise pivaloyl chloride (3.83 mL, 31.1 mmol). The reaction temperature was maintained below −10° C. After the addition was complete, the reaction was kept at −10° C. for 15 min, then was warmed to 0° C. for 10 min, and finally re-cooled to −10° C. 1R,2R-(−)-pseudoephedrine (7.34 g, 44.4 mmol,) was added, and the reaction was stirred at −10° C. for another 10 min, then warmed to RT and stirred for 4 h. Water (30 mL) was added and the mixture was extracted with EtOAc (2×). The combined organic layers were washed with brine, dried (MgSO$_4$), filtered, and concentrated in vacuo to give the crude product. Recrystallization from warm ethyl acetate/hexanes afforded the crystalline product (7.3 g, 75%).

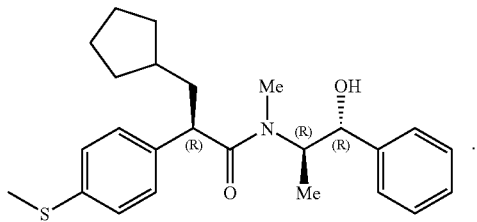

ii

To a solution of LiN(TMS)$_2$ (44.7 mL of a 1M solution in THF, 44.7 mmol) in dry THF (28 mL) was slowly added a solution of 1R,2R-(−)-pseudoephedrine amide 1Ai (7 g, 21.3 mmol) in dry THF (51 mL), while keeping the internal temperature below −65° C. over ~50 min. The reaction was stirred at −70° C. for 15 min, then was warmed to 0° C. for 20 min and re-cooled to −70° C. A solution of cyclo-pentylmethyl iodide (6.70 g, 31.9 mmol) in DMPU (5.4 mL; 44.7 mmol) was added slowly dropwise. The reaction was stirred at −70° C. for 30 min, then was allowed to warm to RT overnight. The reaction mixture was quenched with saturated aqueous NH$_4$Cl (15 mL) and extracted with EtOAc (175 mL). The organic layer was washed with saturated aqueous NH$_4$Cl (50 mL), 2:1 H$_2$O: saturated aqueous NH$_4$Cl (50 mL) and brine (50 mL), dried (MgSO$_4$) and concentrated in vacuo to give the crude product. The crude product was chromatographed (SiO$_2$; EtOAc:hexanes; continuous gradient from 30% EtOAc to 100% EtOAc over 120 min) to give compound 1Aii (5.44 g, 62% yield). The less pure fractions were combined and re-chromatographed as before to give a combined batch of 1Aii (6.94 g, 79%).

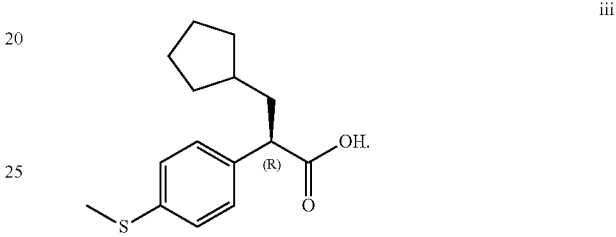

iii

A solution of pseudoephedrine amide 1Aii (5.44 g, 13.22 mmol) in 1,4 dioxane (24 mL) was treated with 9 N aqueous H$_2$SO$_4$ (15 mL). After heating to reflux (bath temperature 105-110° C.) overnight, the reaction mixture was cooled to RT and treated with H$_2$O (100 mL) to completely precipitate the desired product. Filtration and drying afforded the title compound 1Aiii (3.4 g, 97%).

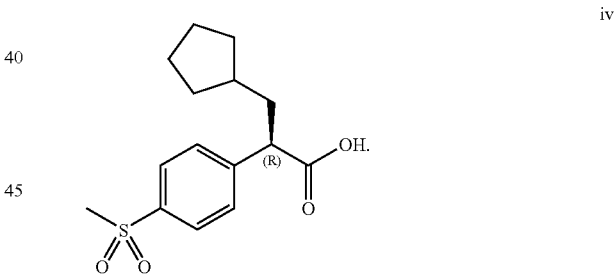

iv

To a solution of acid 1Aiii (3.3 g, 12.5 mmol) in isopropanol (90 mL) and H$_2$O (45 mL) was added oxone (17.6 g, 28.7 mmol). The reaction mixture was stirred at RT overnight, then was concentrated in vacuo to remove the isopropanol. The aqueous layer was extracted with EtOAc (150 mL). The organic layer was washed with water (50 mL) and brine (50 mL), dried (MgSO$_4$), and concentrated in vacuo to give sulfone 1Aiv (3.60 g, 97%) as a white solid.

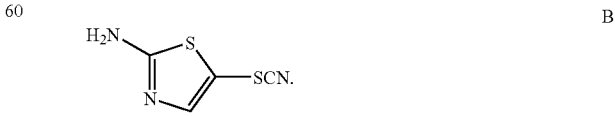

B

To a solution of 2-amino-5-bromothiazole hydrobromide (10.0 g, 38.4 mmol)in MeOH (50 mL) was added KSCN (15.0 g, 160 mmol). The reaction mixture was stirred at RT for 18 h, then was concentrated in vacuo, and H₂O (40 mL) was added to the residue. The mixture was brought to pH 12 with 1N aqueous NaOH. The precipitate was collected by suction filtration, and was washed with H₂O (3×) and Et₂O (3×). The solid was dried under vacuum for 18 h to give Part B compound as a brown solid (2.8 g, 47%).

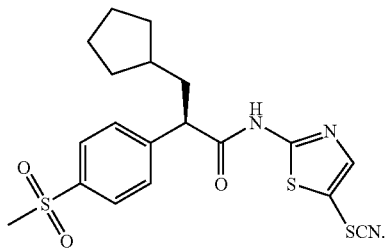

C

To a solution of Part B thiocyanate (800 mg, 5.09 mmol) and acid 1A (1.51 g, 5.09 mmol) in THF (20 mL) was added DEPBT (3.05 g, 10.18 mmol) and iPr₂NEt (1.8 mL, 10.18 mmol). The reaction mixture was stirred at RT for 18 h and then concentrated in vacuo. The residue was taken up in EtOAc, washed with brine, and extracted with EtOAc (3×). The organic layer was washed with 1N aqueous HCl, H₂O, 5% aqueous sodium bicarbonate, H₂O, and brine. The organic layer was dried (MgSO₄), filtered, and concentrated in vacuo. The residue was purified by column chromatography (SiO₂; continuous gradient 10% EtOAc/Hex to 100% EtOAc/Hexane) to give Part C compound (927 mg, 42%) as an orange solid.

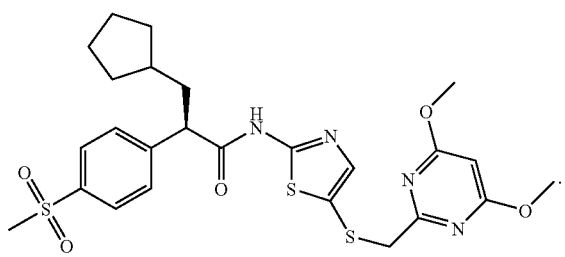

D

To a 0° C. solution of thiocyanate C (30 mg, 0.07mol) in absolute EtOH (1 mL) was added NaBH₄ (5.2 mg, 0.14 mmol). The mixture was stirred at 0° C. for 1 h, after which excess NaBH₄ was cautiously quenched with acetone (1.0 mL), and the mixture was warmed to RT. The mixture was then added to a solution of 2-(chloromethyl)-4,6-dimethoxypyrimidine (17 mg, 0.09 mmol) in absolute EtOH (0.5 mL). The reaction was stirred at RT for 18 h, then was concentrated in vacuo. The residue was purified by preparative HPLC (Phenomenex Luna 5u C18 21.2×100 mm column; detection at 220 nm; flow rate=20 mL/min; continuous gradient from 100% A to 100% B over 8 min+7 min hold time at 100% B, where A=90: 10:0.1 H₂O: MeOH:TFA and B=90:10:0.1 MeOH:H₂O: TFA) to provide the title compound Example 1 (21 mg, 53% yield) as a white solid. [M+H]+=563.1, ¹H NMR (400 MHz, DMSO): δ 7.83 (d, J=8.36 Hz, 2H), 7.57 (d, J=8.44 Hz, 2H), 7.32 (s, 1H), 6.02 (s, 1H), 3.98 (m, 1H), 3.85 (s, 2H), 3.69 (s, 6H), 3.12 (s, 3H), 2.08-1.05 (m, 11H).

Example 2

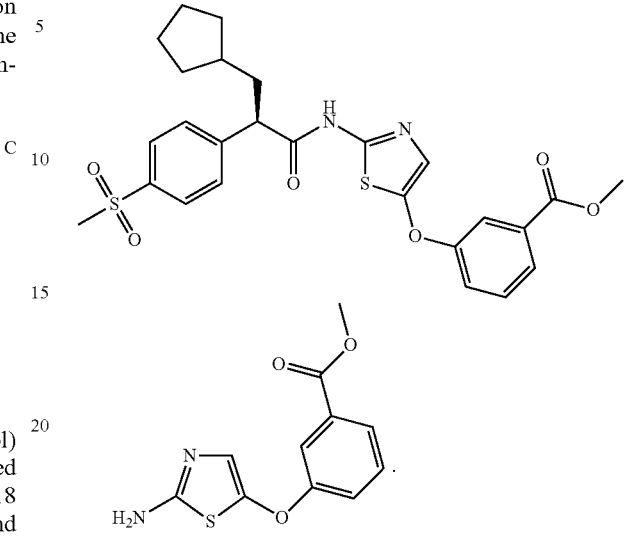

To a RT solution of 5-bromothiazol-2-amine hydrobromide (1.4 g, 5.3 mmol) in acetone (26 mL) was added methyl 3-hydroxybenzoate (888 mg, 5.8 mmol) and cesium carbonate (3.8 g, 11.7 mmol). The reaction mixture was stirred at 55° C. for 5 h, then was cooled to RT, and stirred for an additional 10 h at RT. The mixture was filtered and washed with acetone. The combined filtrates were concentrated in vacuo, and the residue was partitioned between EtOAc and H₂O. The organic phase was dried (MgSO₄) and concentrated in vacuo. The residue was partitioned between EtOAC and 1N aqueous NaOH; the organic phase was washed with brine, dried (MgSO₄), and concentrated in vacuo to provide the crude product A as an oil (445 mg, 34%).

B

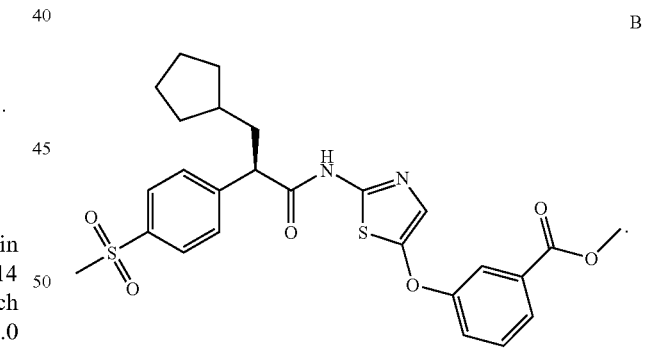

To a solution of Example 1A acid (480 mg, 1.6 mmoL) in CH₂Cl₂ (4 mL) was added oxalyl chloride in CH₂Cl₂ (0.89 mL of a 2.0 M solution; 1.8 mmol). The mixture was stirred at RT for 1 h, then was concentrated in vacuo. The residue was diluted with THF (3 mL), and a solution of Part A compound (445 mg, 1.8 mmol) and pyridine (0.33 mL, 4.1 mmol) in THF (2 mL) was slowly added. The resulting mixture was stirred at RT for 3 h, then was partitioned between EtOAc and H₂O. The organic phase was washed with brine, dried (MgSO₄), and concentrated in vacuo. The residue was purified by preparative HPLC (Phenomenex Luna 5u C18 21.2×100 mm column; detection at 220 nm; flow rate=20 mL/min; continuous gradient from 30% B to 100% B over 8 min+7 min hold time at 100% B, where A=90: 10:0.1 H₂O:MeOH:TFA and B=90: 10:0.1 MeOH:H₂O:TFA) to provide the title compound (188 mg, 55% yield) as a pale yellow solid. [M+H]⁺= 529.2, ¹H NMR(400 MHz, CDCl₃) δ 9.68 (s, 1 H), 7.91 (d, J=7.91 Hz, 2 H), 7.79 (d, J=7.47 Hz, 1 H), 7.70 (s, 1 H), 7.53 (d, J=7.91 Hz, 2 H), 7.40 (t, J=7.91 Hz, 1H), 7.26-7.32 (m, 1 H), 7.09 (s, 1 H), 3.89 (s, 3 H), 3.68 (t, J=7.47 Hz, 1 H), 3.07 (s, 3 H), 2.14-2.31 (m, 1 H), 1.83-1.97 (m, 1 H), 1.67-1.82 (m, 2 H), 1.58-1.67 (m, 3 H), 1.41-1.53 (m, 2 H), 1.02-1.18 (m, 2 H).

Example 3

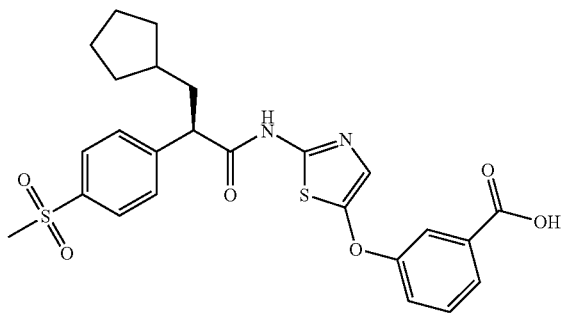

A solution of Example 2 compound (188 mg, 0.4 mmol) in 20% HCl/HOAc (5 mL) was stirred at 80° C. for 16 h. The reaction mixture was cooled to RT, then was partitioned between EtOAc and H₂O. The organic phase was washed with brine, dried (MgSO₄) and concentrated in vacuo. The residue was purified by preparative HPLC (Phenomenex Luna 5u C18 21.2×100 mm column; detection at 220 nm; flow rate=20 mL/min; continuous gradient from 50% B to 100% B over 8 min+7 min hold time at 100% B, where A=90: 10:0.1 H₂O:MeOH:TFA and B=90:10:0.1 MeOH:H₂O:TFA) to provide the title compound (131 mg, 72% yield) as a white solid. [M+H]⁺=515.2, ¹H NMR (400 MHz, CDCl₃) δ 7.91 (d, J=7.47 Hz, 1 H), 7.87 (d, J=8.35 Hz, 2 H), 7.67-7.71 (m, 1 H), 7.62 (d, J=8.35 Hz, 2 H), 7.49 (t, J=7.91Hz, 1 H), 7.38 (dd, J=7.91, 2.20 Hz, 1 H), 7.01 (s, 1 H), 3.85 (t, J=7.47 Hz, 1 H), 3.01 (s, 3 H), 2.17-2.29 (m, 1 H), 1.86-1.97 (m, 1 H), 1.69-1.82 (m, 2 H), 1.52-1.68 (m, 3 H), 1.40-1.50 (m, 2 H), 1.07-1.23 (m, 2 H).

Example 4

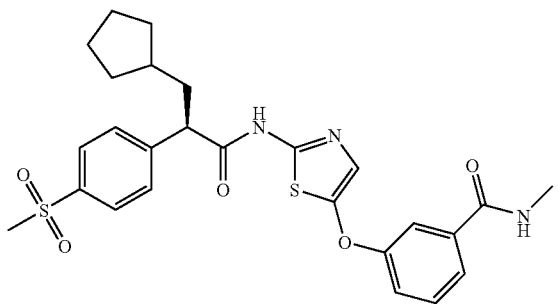

To a solution of Example 3 compound (8 mg, 0.016 mmol) in CH₃CN (0.6 mL) was added methylamine (16 μL of a 2.0 M solution in THF, 0.031 mmol), benzotriazol-1-yloxytris(dimethylamine)phosphorium hexafluorophosphate (14 mg, 0.031 mmol) and iPr₂NEt (5.4 μL, 0.031 mmol). The reaction mixture was stirred at RT for 18 h, then was partitioned between EtOAc and H₂O. The organic phase was washed with brine, dried (MgSO₄) and concentrated in vacuo. The residue was purified by preparative HPLC (Phenomenex Luna 5u C18 21.2×100 mm column; detection at 220 nm; flow rate=20 mL/min; continuous gradient from 30% B to 100% B over 8 min+7 min hold time at 100% B, where A=90: 10:0.1 H₂O:MeOH:TFA and B=90:10:0.1 MeOH:H₂O:TFA) to provide the title compound (5 mg, 61% yield) as a white solid. [M+H]⁺=528.2, ¹H NMR (400 MHz, CDCl₃) δ 7.90 (d, J=8.35 Hz, 2 H), 7.58 (d, J=8.35 Hz, 2 H), 7.49-7.53 (m, 1 H), 7.44-7.48 (m, 1 H), 7.41 (t, J=7.69 Hz, 1 H), 7.22 (dd, J=9.89, 1.98 Hz, 1 H), 7.05 (s, 1 H), 3.84 (t, J=7.47 Hz, 1 H), 3.04 (s, 3 H), 2.99 (d, J=4.83 Hz, 3 H), 2.16-2.27 (m, 1 H), 1.85-1.95 (m, 1 H), 1.67-1.82 (m, 2 H), 1.53-1.67 (m, 3 H), 1.42-1.53 (m, 2 H), 1.04-1.20 (m, 2 H).

Example 5

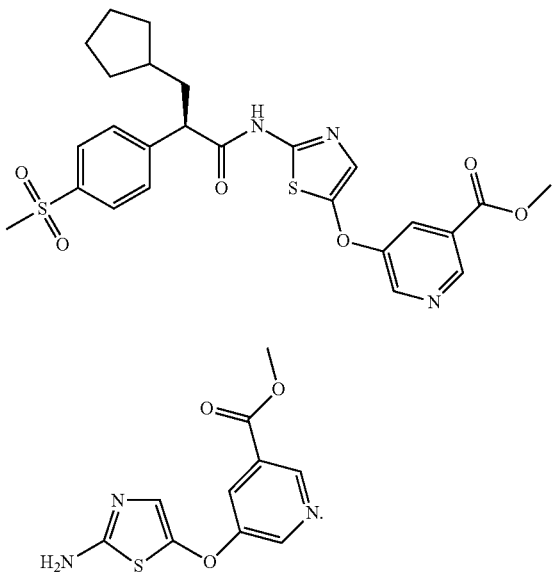

A

To a solution of 5-hydroxynicotinic acid methyl ester (610 mg, 4.0 mmol) in acetone (10 mL), was added 5-bromothiazol-2-amine hydrobromide (2.1 g, 8.0 mmol) and cesium carbonate (3.3 g, 10.0 mmol). The reaction mixture was stirred at reflux for 12 h, then was cooled to RT. The mixture was filtered and washed with acetone. The combined filtrates were concentrated in vacuo, then was partitioned between EtOAc and H₂O. The organic phase was washed with brine, dried (MgSO₄), filtered, and concentrated in vacuo. The residue was purified by preparative HPLC (Phenomenex Luna 5u C18 21.2×100 mm column; detection at 220 nm; flow rate=20 mL/min; continuous gradient from 0% B to 100% B over 8 min+7 min hold time at 100% B, where A=90: 10:0.1 H₂O: MeOH:TFA and B=90: 10:0.1 MeOH:H₂O:TFA) to provide Part A compound (327 mg, 33% yield) as a white solid.

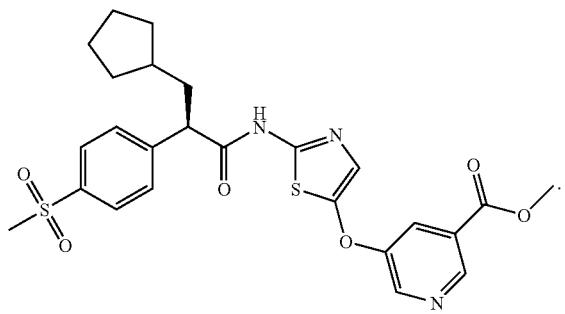

To a solution of Example 1A acid (61 mg, 0.21 mmol) in CH$_2$Cl$_2$ (0.8 mL) was added oxalyl chloride (134 μL of a 2.0 M solution in CH$_2$Cl$_2$, 0.27 mmol) and DMF (2 drops). The mixture was stirred at RT for 90 min, then was concentrated in vacuo. The residue was diluted with THF (1 mL), and Part A thiazole amine (67 mg, 0.27 mmol) and pyridine (33 μL, 0.41 mmol) were added. The reaction mixture was stirred at RT for 2 h, then was partitioned between EtOAc and H$_2$O. The organic phase was washed with brine, dried (MgSO$_4$), and concentrated in vacuo. The residue was purified by preparative HPLC (Phenomenex Luna 5u C18 21.2×100 mm column; detection at 220 nm; flow rate=20 mL/min; continuous gradient from 50% B to 100% B over 8 min+7 min hold time at 100% B, where A=90: 10:0.1 H$_2$O:MeOH:TFA and B=90: 10:0.1 MeOH:H$_2$O:TFA) to provide the title compound (30 mg, 18% yield) as a brown oil. [M+H]$^+$=530.2, $^1$H NMR (400 MHz, CDCl$_3$): δ 9.03 (d, J=1.76 Hz, 1 H), 8.66 (d, J=3.08 Hz, 1 H), 7.84-7.98 (m, 3 H), 7.61 (d, J=8.35 Hz, 2 H), 7.12 (s, 1 H), 3.95 (s, 3 H), 3.86 (t, J=7.69 Hz, 1 H), 3.04 (s, 3 H), 2.16-2.29 (m, 1 H), 1.87-2.02 (m, 1 H), 1.68-1.83 (m, 2 H), 1.55-1.67 (m, 3 H), 1.42-1.54 (m, 2 H), 1.03-1.24 (m, 2 H).

Examples 6 and 7

The following Examples were prepared using the appropriately substituted aromatic/heteroaromatic alcohols according to the general procedure described for the synthesis of Example 5.

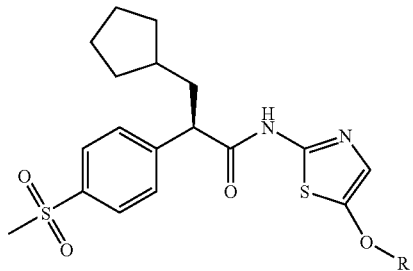

| Example No. | R | [M + H]$^+$ | $^1$H NMR (400 MHz) | Physical Description |
|---|---|---|---|---|
| 6 | 3-pyridyl | 472.2 | δ 8.55 (d, J = 2.64 Hz, 1 H), 8.51 (d, J = 4.83 Hz, 1 H), 7.92 (d, J = 8.35 Hz, 2 H), 7.64 (d, J = 1.76 Hz, 1 H), 7.61 (d, J = 8.35 Hz, 2 H), 7.50-7.56 (m, 1 H), 7.14 (s, 1 H), 3.87 (t, J = 7.69 Hz, 1 H), 3.05 (s, 3 H), 2.16-2.28 (m, 1 H), 1.88-2.00 (m, 1 H), 1.68-1.83 (m, 2 H), 1.55-1.68 (m, 3 H), 1.42-1.55 (m, 2 H), 1.03-1.24 (m, 2 H) | Pale yellow oil |
| 7 | 3-cyanophenyl | 496.1 | δ 7.92 (d, J = 8.35 Hz, 2 H), 7.59 (d, J = 8.35 Hz, 2 H), 7.41-7.51 (m, 2 H), 7.28-7.36 (m, 2 H), 7.10 (s, 1 H), 3.83 (t, J = 7.47 Hz, 1 H), 3.05 (s, 3 H), 2.16-2.30 (m, 1 H), 1.86-1.99 (m, 1 H), 1.68-1.84 (m, 2 H), 1.55-1.68 (m, 3 H), 1.41-1.54 (m, 2 H), 1.03-1.22 (m, 2 H) | White solid |

Example 8

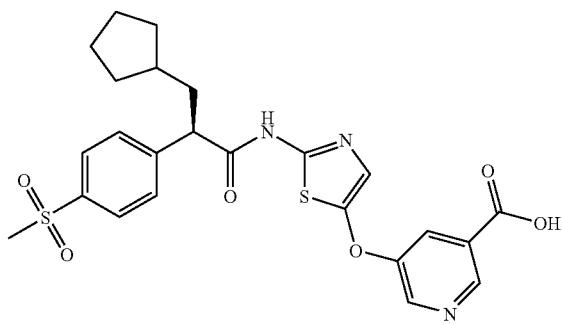

A solution of Example 5 compound (20 mg, 0.038 mmol) in 10% HCl/HOAc (2 mL) was stirred at 80° C. for 15 h. The reaction mixture was partitioned between EtOAc and H₂O. The organic phase was washed with brine, dried (MgSO₄) and concentrated in vacuo. The residue was purified by preparative HPLC (Phenomenex Luna 5u C18 21.2×100 mm column; detection at 220 nm; flow rate=20 mL/min; continuous gradient from 30% B to 100% B over 8 min+7 min hold time at 100% B, where A=90:10:0.1H₂O:MeOH:TFA and B=90:10:0.1 MeOH:H₂O:TFA) to provide the title compound (11.5 mg, 59% yield) as a white solid. [M+H]⁺=516.3, ¹H 1H NMR (400 MHz, CDCl₃) δ 9.10 (d, J=1.76 Hz, 1 H), 8.73 (d, J=2.64 Hz, 1 H), 7.94 (d, J=2.64 Hz, 1 H), 7.88 (d, J=8.35 Hz, 2 H), 7.61 (d, J=8.35 Hz, 2 H), 7.10 (s, 1 H), 3.86 (t, J=7.47 Hz, 1 H), 3.03 (s, 3 H), 2.14-2.31 (m, 1 H), 1.85-1.99 (m, 1 H), 1.69-1.84 (m, 2 H), 1.52-1.69 (m, 3 H), 1.38-1.52 (m, 2 H), 1.01-1.25 (m, 2 H).

Example 9

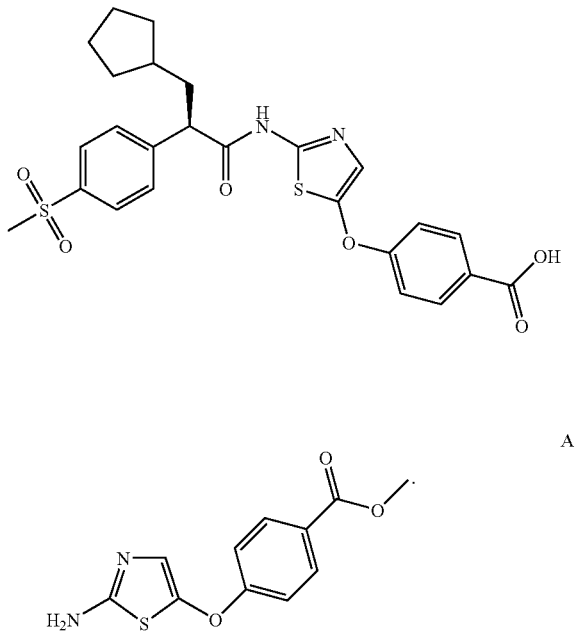

A

To a solution of methyl 4-hydroxybenzoate (175 mg, 1.20 mmol) in acetone (3 mL), was added 5-bromothiazol-2-amine hydrobromide (300 mg g, 1.2 mmol) and cesium carbonate (749 mg, 2.3 mmol). The reaction mixture was stirred at 55° C. for 12 h. The mixture was filtered, and the solids were washed with acetone. The combined filtrates were concentrated in vacuo. The residue was partitioned between EtOAc and H₂O. The organic phase was washed with brine, dried (MgSO₄), filtered, and concentrated in vacuo. The residue was purified by preparative HPLC (Phenomenex Luna 5u C18 21.2×100 mm column; detection at 220 nm; flow rate=20 mL/min; continuous gradient from 0% B to 100% B over 8 min+7 min hold time at 100% B, where A=90:10:0.1 H₂O:MeOH:TFA and B=90: 10:0.1 MeOH:H₂O:TFA) to provide Part A compound (62 mg, 22% yield) as a white solid.

B

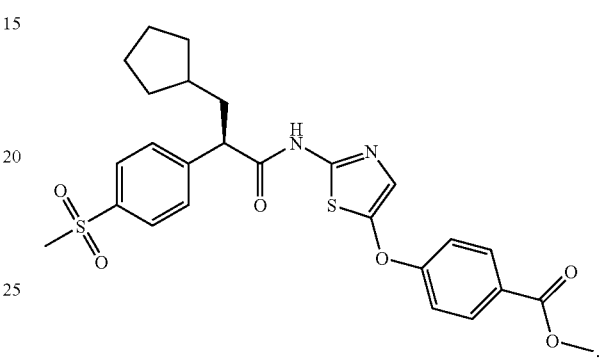

To a solution of Example 1A acid (103 mg, 0.35 mmol) in CH₂Cl₂ (2.0 mL) was added oxalyl chloride (209 μL of a 2.0 M solution in CH₂Cl₂, 0.42 mmol) and DMF (4 drops). The mixture was stirred at RT for 1 h, then was concentrated in vacuo. The residue was diluted with THF (2 mL), and Part A thiazole amine (58 mg, 0.23 mmol) and pyridine (56 μL, 0.67 mmol) were added. The reaction mixture was stirred at RT for 2 h, then was partitioned between EtOAc and H₂O. The organic phase was washed with brine, dried (MgSO₄), and concentrated in vacuo. The residue was purified by preparative HPLC (Phenomenex Luna 5u C18 21.2×100 mm column; detection at 220 nm; flow rate=20 mL/min; continuous gradient from 30% B to 100% B over 8 min+7 min hold time at 100% B, where A=90:10:0.1 H₂O:MeOH:TFA and B=90: 10:0.1 MeOH:H₂O:TFA) to provide the title compound (27 mg, 22% yield) as a brown oil.

C

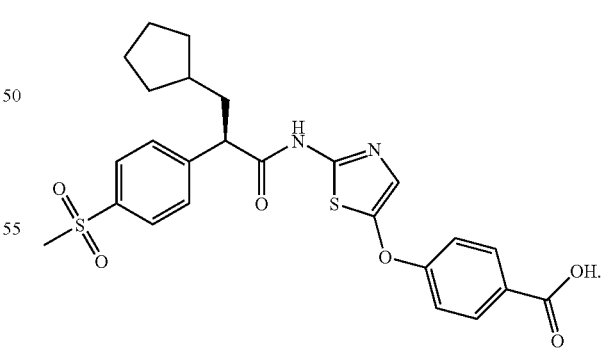

A solution of Part B compound (17.6 mg, 0.033 mmol) in 20% HCl/HOAc (5 mL) was stirred at 80° C. for 16 h. The reaction mixture was cooled to RT, and was partitioned between EtOAc and H₂O. The organic phase was washed with brine, dried (MgSO₄), filtered, and concentrated in vacuo. The residue was purified by preparative HPLC (Phenomenex Luna 5u C18 21.2×100 mm column; detection at 220 nm; flow rate=20 mL/min; continuous gradient from 50% B to 100% B over 8 min+7 min hold time at 100% B, where A=90: 10:0.1 H$_2$O:MeOH:TFA and B=90:10:0.1 MeOH:H$_2$O:TFA) to provide the title compound (11.5 mg, 67% yield) as a white solid). [M+H]$^+$=515.1, $^1$H 1H NMR (400 MHz, CDCl$_3$) δ 8.11 (d, J=8.79 Hz, 2 H), 7.91 (d, J=8.35 Hz, 2 H), 7.64 (d, J=8.35 Hz, 2 H), 7.14 (d, J=9.23 Hz, 2 H), 7.12 (s, 1 H), 3.90 (t, J=7.69 Hz, 1 H), 3.04 (s, 3 H), 2.15-2.33 (m, 1 H), 1.85-2.05 (m, 1 H), 1.69-1.85 (m, 2 H), 1.54-1.70 (m, 3 H), 1.40-1.54 (m, 2 H), 1.02-1.26 (m, 2 H).

Example 10

A

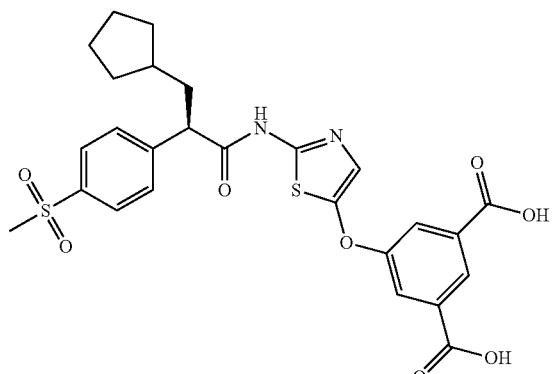

B

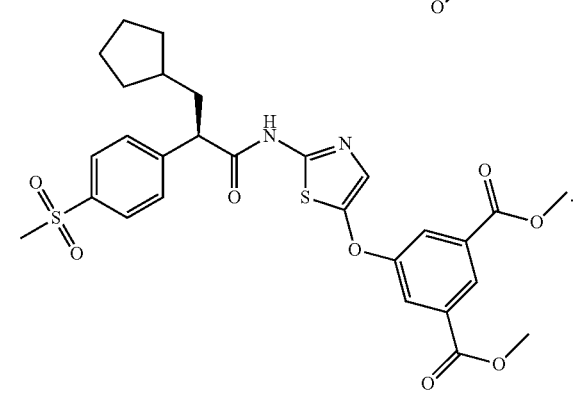

Part A compound was prepared from dimethyl 5-hydroxy-isophthalate and Example 1A acid following the same general procedure used to synthesize Example 5. Part A compound was obtained as a solid (4 mg, 8.4% yield).

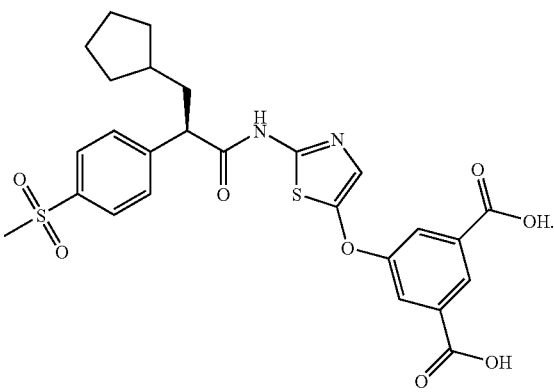

To a solution of the Part A dimethyl ester (16 mg, 0.027 mmol) in THF:H$_2$O (2:1, 1.8 mL) was added LiOH.H$_2$O (5.7 mg, 0.14 mmol). The reaction mixture was stirred at RT for 16 h, then was diluted with EtOAc. The reaction was acidified to pH 1 with 1N aqueous HCl. The organic phase was washed with H$_2$O and brine, dried (MgSO4), and concentrated in vacuo. The residue was purified by preparative HPLC (Phenomenex Luna 5u C18 21.2×100 mm column; detection at 220 nm; flow rate=20 mL/min; continuous gradient from 50% B to 100% B over 8 min+7 min hold time at 100% B, where A=90:10:0.1 H$_2$O:MeOH:TFA and B=90:10:0.1 MeOH:H$_2$O:TFA) to provide the title compound (8.0 mg, 52% yield) as a white solid. [M+H]$^+$=559.7, $^1$H NMR(400 MHz, CD$_3$OD) δ 8.40 (s, 1 H), 7.80-7.97 (m, 3 H), 7.57-7.74 (m, 3 H), 7.11 (s, 1 H), 3.83-4.03 (m, 1 H), 3.08 (s, 3 H), 2.09-2.31 (m, 1 H), 1.74-1.92 (m, 3 H), 1.56-1.74 (m, 3 H), 1.41-1.56 (m, 2 H), 1.05-1.26 (m, 2 H).

Example 11

A

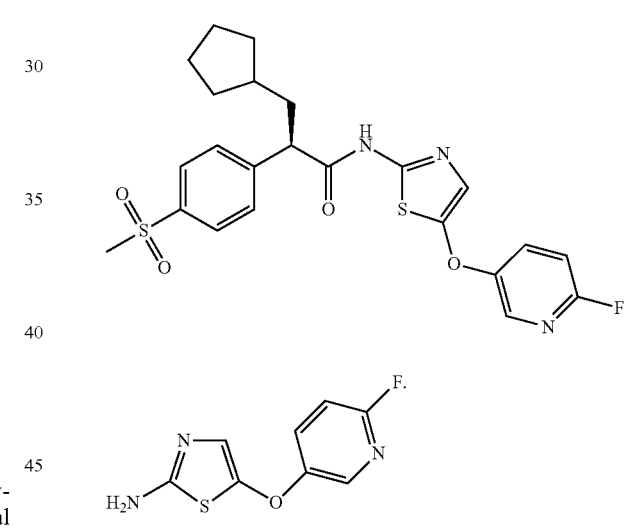

To a solution of 5-bromothiazol-2-amine hydrobromide (100 mg, 0.39 mmol) in acetone (2 mL) was added 2-fluoro-5-hydroxy pyridine (44 mg, 0.39 mmol) and cesium carbonate (251 mg, 0.77 mmol). The reaction mixture was stirred at reflux for 12 h, then was cooled to RT. The mixture was filtered and solids were washed with acetone. The filtrates was concentrated in vacuo. The residue was partitioned between EtOAc and H$_2$O. The organic phase was washed with brine, dried (MgSO$_4$), and concentrated in vacuo. The residue was purified by preparative HPLC (Phenomenex Luna 5u C18 21.2×100 mm column; detection at 220 nm; flow rate=20 mL/min; continuous gradient from 10% B to 100% B over 8 min+7 min hold time at 100% B, where A=90:10:0.1 H$_2$O:MeOH:TFA and B=90:10:0.1 MeOH:H$_2$O:TFA) to provide Part A compound (28 mg, 34%) as a white solid.

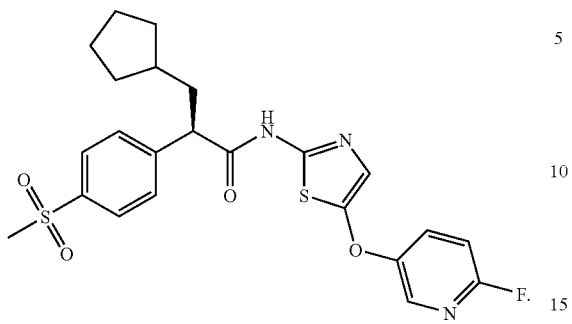

To a solution of the Example 1A acid (19 mg, 0.064 mmol) in CH$_3$CN (1 mL) was added the Part A thiazole-amine (20 mg, 0.096 mmol), benzotriazol-1-yloxytris(dimethylamine) phosphonium hexafluorophosphate (57 mg, 0. 13 mmol), and iPr$_2$Net (22 µL, 0.13 mmol). The reaction mixture was stirred at RT for 24 h, then was partitioned between EtOAc and H$_2$O. The organic phase was washed with brine, dried (MgSO$_4$), filtered, and concentrated in vacuo. The residue was purified by preparative HPLC (Phenomenex Luna 5u C18 21.2×100 mm column; detection at 220 nm; flow rate=20 mL/min; continuous gradient from 30% B to 100% B over 8 min+7 min hold time at 100% B, where A=90:10:0.1 H$_2$O:MeOH:TFA and B=90:10:0.1 MeOH:H$_2$O:TFA) to provide the title compound (6.5 mg, 21% yield) as a pale brown solid. [M+H]$^+$= 490.2, $^1$H NMR(400 MHz, CDCl$_3$) δ 8.01-8.10 (m, 1 H), 7.91 (d, J=8.35 Hz, 2 H), 7.61 (d, J=8.35 Hz, 2 H), 7.49-7.57 (m, 1 H), 7.05 (s, 1 H), 6.96 (dd, J=8.79, 3.52 Hz, 1 H), 3.89 (t, J=7.69 Hz, 1 H), 3.04 (s, 3 H), 2.17-2.29 (m, 1 H), 1.87-2.01 (m, 1 H), 1.68-1.84 (m, 2 H), 1.54-1.68 (m, 3 H), 1.41-1.54 (m, 2 H), 1.04-1.27 (m, 2 H).

Example 12

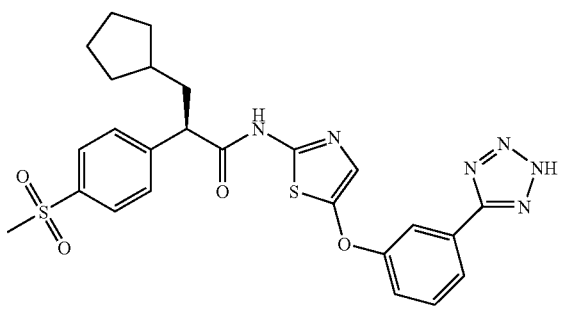

To a solution of Example 7 nitrile (14 mg, 0.028 mmol) in water (0.6 mL) was added NaN$_3$ (6.1 mg, 0.093 mmol) and Zn(Br)$_2$ (19.1 mg, 0.085 mmol). The reaction mixture was stirred at reflux for 17 h, then was cooled to RT, after which 1 N aqueous HCl (2 mL) and EtOAc (5 mL) were added. The reaction was stirred for another 30 min at RT, and the organic layer was isolated. The aqueous layer was extracted with EtOAc (2×5 mL). The combined organic extracts were concentrated in vacuo. The residue was taken up in 1N aqueous NaOH (2 mL), and the mixture was stirred for 30 min at RT. The organic phase was washed with brine, dried (MgSO$_4$) and concentrated in vacuo. The residue was purified by preparative HPLC (Phenomenex Luna 5u C18 21.2×100 mm column; detection at 220 nm; flow rate=20 mL/min; continuous gradient from 50% B to 100% B over 8 min+7 min hold time at 100% B, where A=90:10:0.1 H$_2$O:MeOH:TFA and B=90:10:0.1 MeOH:H$_2$O:TFA) to provide the title compound (2.5 mg, 29% yield) as a white solid. [M+H]$^+$=539.1, $^1$H NMR (500 MHz, CD$_3$OD) δ 7.92 (d, J=8.25 Hz, 2 H), 7.79 (d, J=7.70 Hz, 1 H), 7.74 (s, 1 H), 7.66 (d, J=8.25 Hz, 2 H), 7.56 (t, J=7.97 Hz, 1 H), 7.30 (d, J=8.25 Hz, 1 H), 7.17 (s, 1 H), 4.09 (q, J=7.15 Hz, 1 H), 3.95 (s, 1 H), 3.09 (s, 3 H), 2.13-2.27 (m, 1 H), 1.75-1.91 (m, 3 H), 1.58-1.73 (m, 3 H), 1.52 (dd, J=6.87, 4.67 Hz, 2 H), 1.11-1.25 (m, 2 H).

Example 13

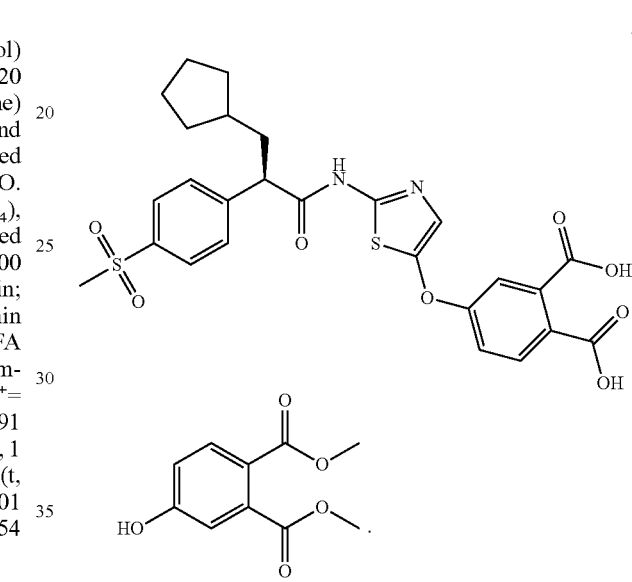

To a solution of 4-hydroxyphthalic acid (1.04 g, 5.71 mmol) in MeOH (11.4 mL) was slowly added TMSCHN$_2$ (6.28 mL, 12.56 mmol). The reaction mixture was stirred at RT for 15 h, then was concentrated in vacuo. The residue was partitioned between EtOAc and H$_2$O. The organic phase was washed with brine, dried (MgSO$_4$), and concentrated in vacuo. The crude residue was chromatographed (SiO$_2$; continuous gradient from 0% EtOAc/Hexane to 100% EtOAc/Hexane) to provide Part A compound (150 mg, 13%) as a solid.

To a solution of 5-bromothiazol-2-amine hydrobromide (278 mg, 1.07 mmol) in acetone (5.4 mL) was added Part A dimethyl ester (150 mg, 0.74 mmol) and cesium carbonate (465 mg, 1.43 mmol). The reaction mixture was stirred at 55° C. for 16 h, then was cooled to RT. The reaction mixture was filtered and washed with acetone; the combined filtrates were concentrated in vacuo. The residue was partitioned between EtOAc and H₂O. The organic phase was washed with brine, dried (MgSO₄), filtered, and concentrated in vacuo. The residue was purified by preparative HPLC (Phenomenex Luna 5u C18 21.2×100 mm column; detection at 220 nm; flow rate=20 mL/min; continuous gradient from 0% B to 100% B over 8 min+7 min hold time at 100% B, where A=90:10:0.1 H₂O:MeOH:TFA and B=90:10:0.1 MeOH:H₂O:TFA) to provide Part B compound (144 mg, 65% yield) as a solid.

C

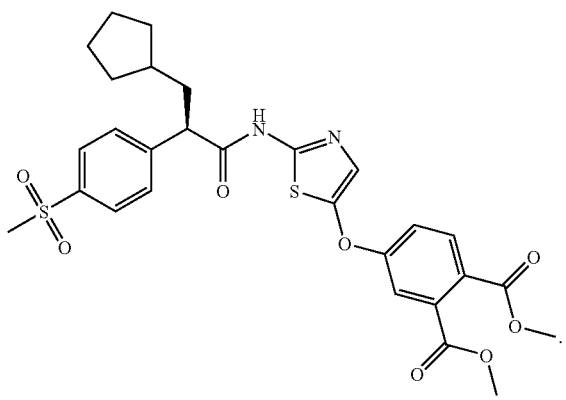

To a solution of Example 1A acid (68.5 mg, 0.232 mmol) in CH₂Cl₂ (1.5 mL) was added oxalyl chloride (174 μL, 0.348 mmol, 2.0 M in CH₂Cl₂) and DMF (3 drops). The reaction mixture was stirred at RT for 1 h, then was concentrated in vacuo. The residue was taken up in THF (0.6 mL), and the resulting solution was added to a solution of Part B compound (51 mg, 0.166 mmol) and NaHCO₃ (42 mg, 0.498 mmol) in THF:H₂O (1:1, 1.2 mL). The reaction mixture was stirred at RT for 2 h, then was partitioned between EtOAc and H₂O. The organic phase was washed with brine, dried (MgSO₄), and concentrated in vacuo. The residue was purified by preparative HPLC (Phenomenex Luna 5u C18 21.2×100 mm column; detection at 220 nm; flow rate=20 mL/min; continuous gradient from 50% B to 100% B over 8 min+7 min hold time at 100% B, where A=90:10:0.1 H₂O:MeOH:TFA and B=90:10:0.1 MeOH:H₂O:TFA) to provide Part C compound (53 mg, 54% yield) as a white solid.

D

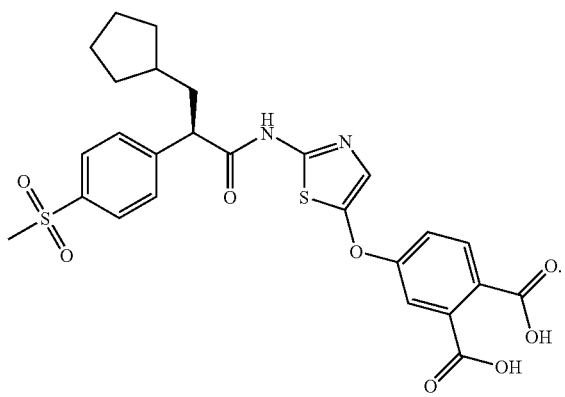

To a solution of Part C dimethyl ester (47 mg, 0.080 mmol) in THF:H₂O (2:1, 3 mL) was added LiOH.H₂O (16.8 mg, 0.40 mmol). The reaction was stirred at RT for 16 h, then was diluted with EtOAc. The reaction was acidified to pH 1-2 with 1N aqueous HCl. The organic phase was washed with H₂O and brine, dried (MgSO₄), and concentrated in vacuo. The residue was purified by preparative HPLC (Phenomenex Luna 5u C18 21.2×100 mm column; detection at 220 nm; flow rate=20 mL/min; continuous gradient from 50% B to 100% B over 8 min+7 min hold time at 100% B, where A=90:10:0.1H₂O:MeOH:TFA and B=90:10:0.1 MeOH:H₂O:TFA) to provide the title compound (27 mg, 60% yield) as a white solid. [M+H]⁺=559.6, ¹H NMR(400 MHz, CD₃OD) δ 7.92 (d, J=8.35 Hz, 2 H), 7.82 (d, J=8.79 Hz, 1 H), 7.67 (d, J=8.35 Hz, 2 H), 7.29 (d, J=2.64 Hz, 1 H), 7.23 (dd, J=8.35, 2.64 Hz, 1 H), 7.17 (s, 1 H), 3.90-4.00 (m, 1 H), 3.09 (s, 3 H), 2.12-2.28 (m, 1 H), 1.74-1.91 (m, 3 H), 1.58-1.73 (m, 3 H), 1.44-1.58 (m, J=7.25, 4.61 Hz, 2 H), 1.09-1.25 (m, 2 H).

Example 14

A

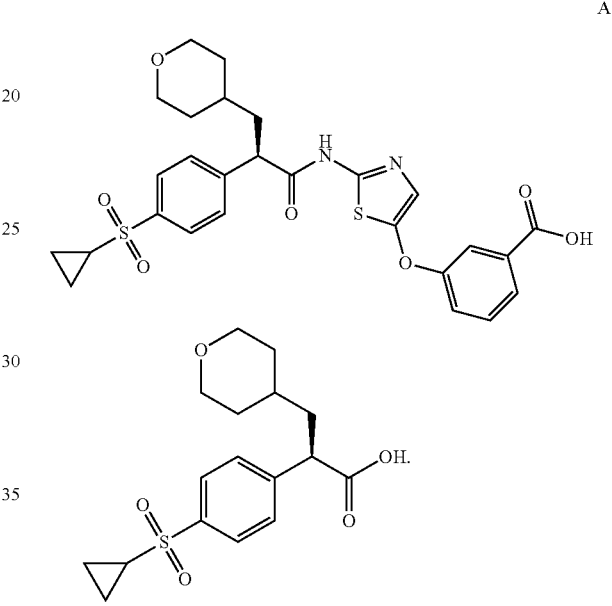

Note: The following procedure was adapted from WO 2006/016178 and WO 2006/016174.

i

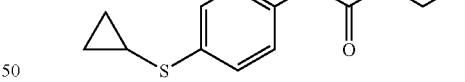

Aluminum chloride (8.44 g, 63.3 mmol) was suspended in dichloromethane (40 ml) and was cooled to 0° C. via an ice bath with stirring. Ethyl 2-chloro-2-oxoacetate (5.53 ml, 49.7 mmol) was added over a period of 10 min at 0° C. The reaction was stirred at 0° C. for 30 min. Cyclopropyl phenyl sulfide (6.5 ml, 45.2 mmol) was then added over a period of 45 min, keeping the temperature at 0° C. [Note: when sulfide was added, reaction immediately turned deep purple/red in color] The reaction was allowed to warm to RT and was stirred at RT for 18 h. Ice water (100 mL) was slowly added to the mixture while being cooled in an ice bath. The organic layer was separated and washed with H₂O (2×), saturated aqueous NaHCO₃ (2×), and again with H₂O (1×). The organic layer was dried [MgSO₄], filtered, and concentrated in vacuo to give crude Part A(i) compound (6.1 g, 54% yield) as a yellow oil.

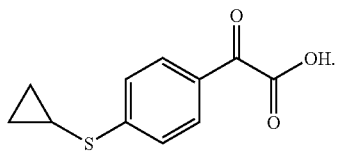

ii

A solution of the Part A(i) compound (6.1 g, 24.37 mmol) in Toluene (50 ml) was heated to 50° C. with stirring. 3N aqueous sodium hydroxide (9.75 ml, 29.2 mmol) was then added dropwise via a dropping funnel while keeping the temperature below 60° C. After the addition was complete, the reaction was stirred at 50° C. for several hours. The reaction was then cooled to RT and was treated dropwise with concentrated hydrochloric acid (0.821 ml, 26.8 mmol). The reaction was stirred at RT for 18 h. No solid precipitated out, so the layers were separated. The organic layer was concentrated in vacuo to give the crude Part A(ii) compound (6.0g, 111% yield) as a yellow solid.

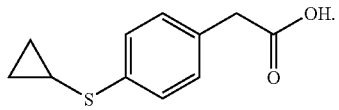

iii

A reaction flask was charged with hydrazine monohydrate (5.89 mL, 121 mmol) and was cooled to −78° C. The Part A(ii) compound (5.4 g, 24.30 mmol) was added in one portion, and the reaction was heated to 80° C. with stirring. After reaching 80° C., the heat was removed and KOH (0.818 g, 14.58 mmol) was added. The reaction was stirred at RT for several minutes, and then a second portion of KOH (0.818 g, 14.58 mmol) was added. The reaction was stirred at RT for several minutes, and then a third portion of KOH (0.818 g, 14.58 mmol) was added. The reaction again was stirred at RT for several minutes, and a fourth portion of KOH (0.818 g, 14.58 mmol) was added. The reaction was then heated at 100° C. with stirring for 18 h. The reaction was cooled to RT and was diluted with H₂O. The reaction mixture was washed with diethyl ether and H₂O. The layers were separated, and the aqueous layer was transferred to a round bottom flask. The organic layer was washed with H₂O, and the aqueous layers were combined. The aqueous layer was treated with heptane (~50 mL), and the mixture was stirred vigorously. The stirred solution was treated dropwise with concentrated HCl (11.66 mL, 384 mmol) over 30 min at 0° C. (via an ice bath). The suspension was warmed to RT and was stirred at RT for 3 h. A precipitate formed and was filtered off. The yellow precipitate was washed with 1N aqueous HCl and heptane and was dried under vacuum for 48 h.

The Part A(iii) compound (3.7g, 73% yield) was isolated as a pale yellow solid

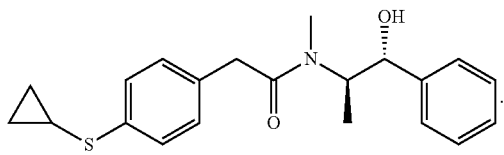

iv

The Part A(iii) compound was evaporated with toluene (2×). A mixture of the Part A(iii) compound (3.7 g, 17.76 mmol) and Potassium Carbonate (7.37 g, 53.3 mmol) in anhydrous Acetone (50 ml) was cooled to −10° C. The slurry was then treated dropwise with Trimethylacetyl chloride (2.297 ml, 18.65 mmol), while maintaining the temperature below −10° C. The reaction was stirred at −10° C. for 30 min and was then warmed to 0° C. for 1 h. The reaction was then warmed to RT for 30 min. The mixture was recooled to −10° C. and was treated with (1R,2R)-(−)-pseudoephedrine (4.40 g, 26.6 mmol). The reaction was stirred at −10° C. for 1 h and was then warmed to 25° C. and was stirred for 18 h. The reaction was quenched with H₂O (25 mL) and was extracted with EtOAc. The organic layer was washed with 1N aqueous HCl, was dried [MgSO4], filtered, and concentrated in vacuo to give the crude Part D compound. The crude Part D compound was dissolved in dichloromethane and purified by column chromatography (120 g ISCO column; isocratic ISCO 30% EtOAc/Hexane to 100% EtOAc). The product fractions were combined and concentrated in vacuo to give the Part A(iv) compound (1.16 g, 18.4% yield) as a white solid.

v

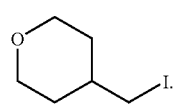

a

To a solution of tetrahydropyran-4-methanol (5.0 g, 43 mmol) in dichlormethane (30 mL) was added triethylamine (7.2 mL, 51.6 mmol). The mixture was cooled to 0° C., and methane sulfonyl chloride (4.0 mL, 51.6 mmol) was added. The mixture was stirred in an ice bath for several hours and was slowly warmed to RT. The reaction then was stirred at RT for 18 h. The reaction was concentrated in vacuo. The residue was taken up in EtOAc and was washed with saturated NaHCO₃. The organic layer was dried [MgSO₄], filtered, and concentrated in vacuo to give the mesylate Part A(v)(a) compound (8.3 g, quantitative yield) as a white, needle-like solid.

b

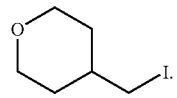

A mixture of the mesylate Part A(v)(a) compound (8.3 g, 43.0 mmol) and sodium iodide (12.8 g, 85.5 mmol) was refluxed at 65° C. in acetone (100 mL) for 18 h. The reaction mixture was cooled to RT and was filtered. The filter cake was washed with acetone. The filtrate was concentrated in vacuo, and the residue was partitioned between diethyl ether and water. The layers were separated, and the aqueous layer was washed with ether. The combined organic layers were washed with 10% aqueous sodium thiosulfate solution and then with water. The organic layer was dried [MgSO₄], filtered, and concentrated in vacuo to give the iodide Part A(v)(b) compound (7.1 g, 74% yield) as a yellow oil.

vi

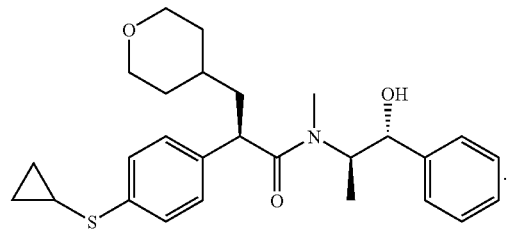

All starting materials were evaporated with toluene several times and all glassware was dried in oven overnight.

A solution of LiHMDS (5.91 ml, 5.91 mmol) in THF (15 ml) was cooled to −78° C. The acetamide Part A(iv) compound(1.0 g, 2.81 mmol) was dissolved in THF (15 ml) and was added dropwise to the LiHMDS solution over 15 min. The reaction was stirred at −78° C. for 15 min and was then warmed to 0° C. for 45 min. The reaction was recooled to −78° C., and distilled DMPU (0.714 ml, 5.91 mmol) was added; the reaction was stirred at −78° C. for about 15 min, then the iodide Part A(v) compound (0.954 g, 4.22 mmol) was added. The reaction was stirred at −78° C. for 1 h and was then slowly warmed to RT and was stirred for 18 h. The reaction was quenched with saturated aqueous NH₄Cl (~10 mL) and was diluted with EtOAc. The reaction was washed with H₂O. The aqueous layer was extracted with EtOAc, and the combined organic layers were washed with Brine, dried [MgSO₄], filtered, and concentrated in vacuo to give the Part A(vi) compound (1.3 g, quantitative yield) as a yellow oil.

vii

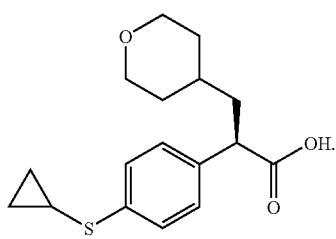

A solution of Part A(vi) compound(1.3 g, 2.87 mmol) and 9N concentrated sulfuric acid (10.4 ml, 94 mmol) in dioxane (20 ml) was refluxed at 110° C. for 18 h. The reaction was cooled to RT, diluted with EtOAc (50 mL), and was washed with H₂O (40 mL×2) and brine (20 mL). The organic layer was dried [MgSO₄], filtered, and concentrated in vacuo to give the acid Part A(vii) compound (1.17 g, 133% yield) as a yellow, sticky oil.

viii

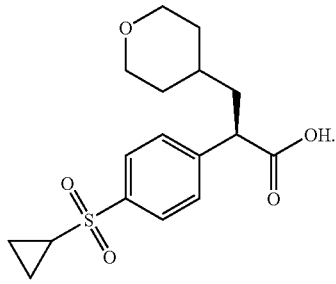

To a solution of the acid Part A(vii) compound(0.9 g, 2.94 mmol) in isopropanol (20 ml) and water (10.00 ml) was added oxone (4.15 g, 6.76 mmol). The reaction was stirred at RT for 18 h. The reaction was filtered, and the filtrate was concentrated in vacuo. The residue was taken up in EtOAc and was washed with H₂O and Brine. The organic layer was dried [MgSO₄], filtered, and concentrated in vacuo to give the Part A(viii) compound (0.9 g, 91% yield) as a pale-yellow foam.

B

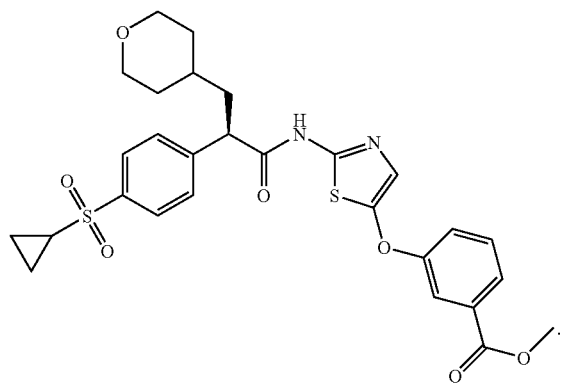

To a 0° C. solution of the Part A acid (96 mg, 0.28 mmol) in dichloromethane (4 ml) was added oxalyl chloride (2M in DCM, 0.21 ml, 0.42 mmol) and DMF (0.1 ml). The resulting mixture was stirred at RT for 90 min. The acid chloride was then concentrated in vacuo. The acid chloride residue was taken up in tetrahydrofuran (3 ml), and Example 2A amine (78 mg, 0.31 mmol) and pyridine (0.09 mL, 1.13 mmol) were added. The reaction was stirred at RT for 18 h. The reaction mixture was diluted with EtOAc and was washed with water and brine. The organic layer was dried (MgSO₄), filtered, and concentrated in vacuo. The residue was purified by preparative HPLC (Phenomenex Luna AX1A 5u C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to give the Part B compound (60 mg, 37% yield) as an off white lyophilate.

C

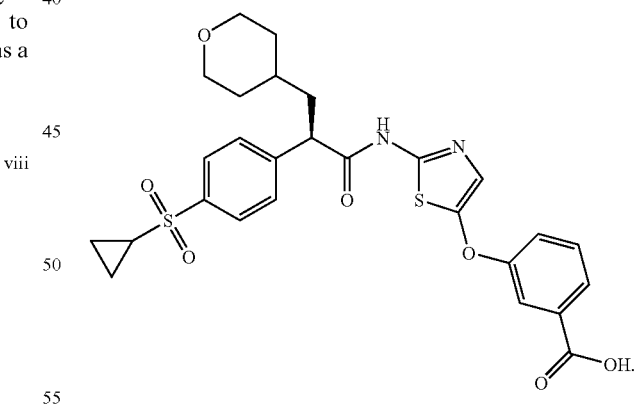

To a solution of the Part B compound (60 mg, 0.11 mmol) in THF:H₂O (2:1, 3 mL) was added lithium hydroxide (12.6 mg, 0.53 mmol). The reaction was stirred at RT for 18 h. The reaction was diluted with EtOAc and was acidified with 1N aqueous HCl to pH 1-2. The mixture was washed with H₂O and Brine. The organic layer was dried (MgSO4), filtered, and concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to give the title compound (38.9 mg, 67% yield) as a white solid. [M+H]⁺=557.1, ¹HNMR(400 MHz, CDCl₃) δ 7.94-7.20 (m, 9H), 4.22 (m, 1H), 3.91 (m, 2H), 3.28 (m, 2H), 2.45 (m, 1H), 2.20 (m, 1H), 1.63 (m, 2H), 1.33 (m, 6H), 1.01 (m, 2H).

Example 15

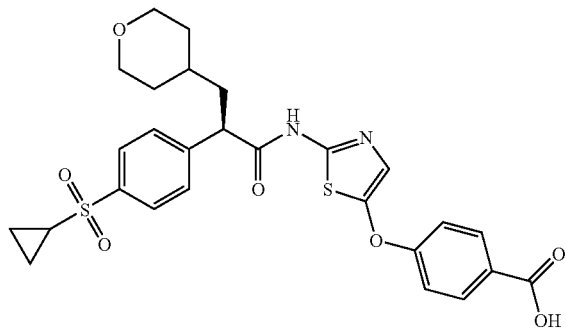

The title compound (32.6 mg, 21% yield, white solid) was prepared from Example 9A amine (78 mg, 0.31 mmol) following the same general procedure used to prepare Example 14. [M+H]⁺=557.2, ¹HNMR(400 MHz, CDCl₃) δ 8.15-7.15 (m, 9H), 4.22 (m, 1H), 3.91 (m, 2H), 3.28 (m, 2H), 2.45 (m, 1H), 2.20 (m, 1H), 1.63 (m, 2H), 1.35 (m, 6H), 1.04 (m, 2H).

Example 16

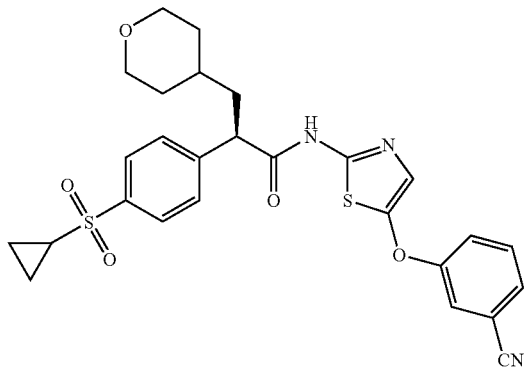

A

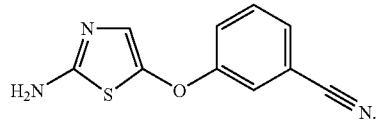

To a solution of 3-hydroxybenzonitrile (137 mg, 1.15 mmol) in acetone (3 mL), was added 5-bromothiazol-2-amine hydrobromide (300 mg, 1.15 mmol) and Cs₂CO₃ (749 mg, 2.30 mmol). The reaction mixture was stirred at 55° C. for 12 h, then was cooled to RT. The mixture was filtered and washed with acetone. The combined filtrates were concentrated in vacuo, then partitioned between EtOAc and H₂O. The organic phase was washed with brine, dried (MgSO₄), filtered, and concentrated in vacuo. The residue was purified by preparative HPLC (Phenomenex Luna 5u C18 21.2×100 mm column; detection at 220 nm; flow rate=20 mL/min; continuous gradient from 0% B to 100% B over 8 min+7 min hold time at 100% B, where A=90:10:0.1 H₂O:MeOH:TFA and B=90:10:0.1 MeOH:H₂O:TFA) to provide Part A compound (70 mg, 28% yield) as a solid.

B

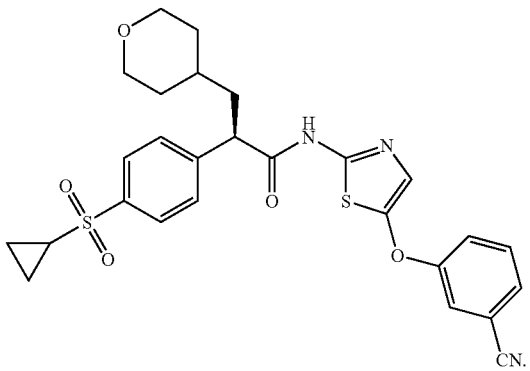

To a 0° C. solution of the Example 14 Part A acid (330 mg, 0.98 mmol) in dichloromethane (10 ml) was added oxalyl chloride (2M in DCM, 0.8 ml, 1.46 mmol) and DMF (0.1 ml). The resulting mixture was stirred at 0° C. for 30 min and was then warmed to RT and was stirred for 90 min. The acid chloride was then concentrated in vacuo. The acid chloride residue was taken up in tetrahydrofuran (10 ml), and Part A amine (233 mg, 1.07 mmol) and pyridine (0.32 mL, 3.90 mmol) were added. The reaction was stirred at RT for 18 h. The reaction mixture was diluted with EtOAc and was washed with water and brine. The organic layer was dried (MgSO₄), filtered, and concentrated in vacuo. The residue was purified by preparative HPLC (Phenomenex Luna AXIA 5u C18 30×100 mm column; detection at 220 nm; flow rate=40 mL/min; continuous gradient from 30% B to 100% B over 10 min+5 min hold time at 100% B, where A=90:10:0.1 H₂O:MeOH:TFA and B=90:10:0.1 MeOH:H₂O:TFA) to give the title compound (161 mg, 31% yield) as yellow oil. [M+H]⁺=538.1, ¹HNMR(400 MHz, CDCl₃) δ 7.76-7.02 (m, 9H), 3.98 (m, 1H), 3.74 (m, 2H), 3.20 (m, 2H), 2.53 (m, 1H), 2.03 (m, 1H), 1.90-0.89 (m, 10H).

Example 17

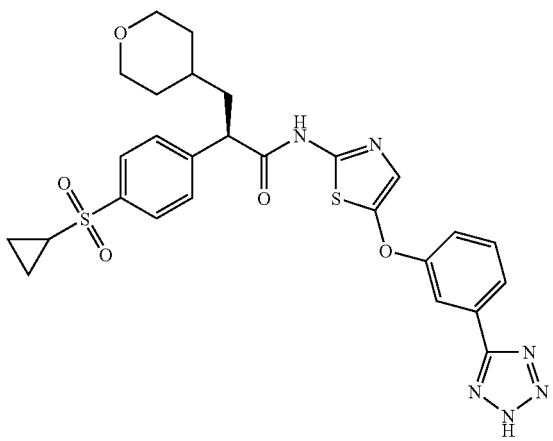

The title compound was prepared from Example 16 (73 mg, 0.14 mmol) following the same general procedure used to prepare Example 12 to give a white lyophilate (17 mg, 22% yield). [M+H]⁺=581.3, ¹H NMR(400 MHz, CDCl₃) δ 7.79-

7.07 (m, 9H), 3.95 (m, 1H), 3.80 (m, 2H), 3.20 (m, 2H), 2.55 (m, 1H), 2.03 (m, 1H), 1.69-0.95 (m, 10H).

Example 18

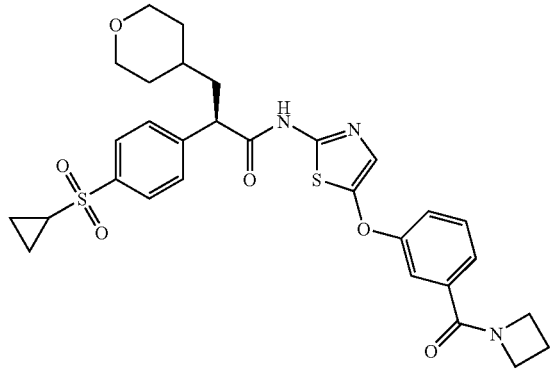

To a solution of the Example 14 acid (40 mg, 0.072 mmol), azetidine hydrochloride (8.74 mg, 0.093 mmol), and HOAt (12.23 mg, 0.090 mmol) in DMF (2 ml) were added Hunig's Base (0.033 ml, 0.187 mmol) and EDAC (17.2 mg, 0.090 mmol). The reaction was stirred at 25° C. for 18 h, then was concentrated in vacuo. The residue was purified by preparative HPLC (Phenomenex Luna AXIA 5 µm C18 30×100 mm column; detection at 220 nm; flow rate=40 mL/min; continuous gradient from 30% B to 100% B over 10 min+2 min hold time at 100% B, where A=90:10:0.1 H$_2$O:MeOH:TFA and B=90:10:0.1 MeOH:H$_2$O:TFA) to give the title compound (25 mg, 58% yield) as a white solid lyophilate. [M+H]$^+$=596.4, $^1$H NMR(500 MHz, MeOH-d$_4$) δ 7.88 (m, 2H), 7.66 (m, 2H), 7.44 (m, 1H), 7.40 (m, 1H), 7.31 (m, 1H), 7.21 (m, 1H), 7.11 (s, 1H), 4.32 (m, 2H), 4.16 (m, 2H), 4.03 (m, 1H), 3.91 (m, 2H), 3.30 (m, 2H), 2.66 (m, 1H), 2.34 (m, 2H), 2.16 (m, 1H), 1.78 (m, 1H), 1.67 (m, 2H), 1.65-1.21 (m, 5H), 1.04 (m, 2H).

Example 19

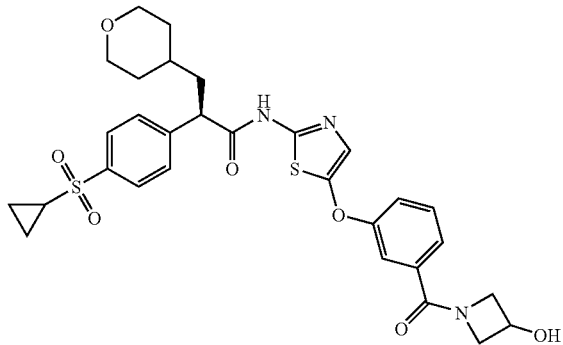

The title compound (20 mg, 46% yield, white solid) was prepared from azetidin-3-ol hydrochloride (10.23 mg, 0.093 mmol) following the same general procedure used to prepare Example 18. [M+H]$^+$=612.4, $^1$H NMR(500 MHz, MeOH-d$_4$) δ 7.89 (m, 2H), 7.66 (m, 2H), 7.45 (m, 1H), 7.40 (m, 1H), 7.31 (m, 1H), 7.25 (m, 1H), 7.12 (s, 1H), 4.58 (m, 1H), 4.48 (m, 1H), 4.35 (m, 1H), 4.03 (m, 2H), 3.89 (m, 3H), 3.30 (m, 2H), 2.66 (m, 1H), 2.16 (m, 1H), 1.78 (m, 1H), 1.67 (m, 2H), 1.45-1.21 (m, 5H), 1.04 (m, 2H).

Example 20

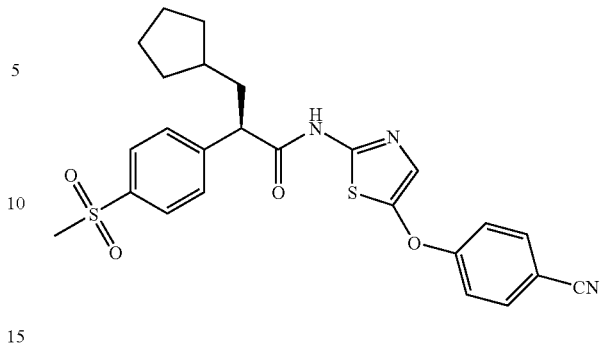

The title compound (35 mg, 21% yield, yellow solid) was prepared following the procedure set forth in Example 7. [M+H]+=496.1, $^1$H NMR (400 MHz, MeOH-d$_4$) δ 7.90 (2 H, d, J=8.79 Hz), 7.70 (2 H, d, J=9.23 Hz), 7.65 (2 H, d, J=8.35 Hz), 7.19 (2 H, d, J=8.79 Hz), 7.15 (1 H, s), 3.93 (1 H, t, J=7.69 Hz), 3.08 (3 H, s), 2.12-2.26 (1 H, m), 1.72-1.89 (3 H, m), 1.56-1.71 (3 H, m), 1.43-1.55 (2 H, m), 1.06-1.25 (2 H, m)

Example 21

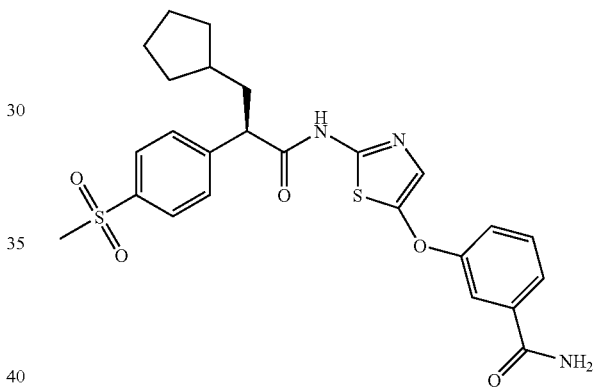

To a solution of Example 7 compound (40 mg, 0.081 mmol) in THF (2 mL) was added 1N aqueous NaOH (1 mL). The reaction was stirred at 60° C. for 3 h, then was cooled to RT. The mixture was diluted with EtOAc, and was washed with H$_2$O and brine. The organic layer was dried (MgSO$_4$), and concentrated in vacuo. The residue was purified by preparative HPLC (Phenomenex Luna AXIA 5u C18 30×100 mm column; detection at 220 nm; flow rate=40 mL/min; continuous gradient from 40% B to 100% B over 10 min, where A=90:10:0.1 H$_2$O:MeOH:TFA and B=90:10:0.1 MeOH:H$_2$O:TFA) to provide the title compound (22 mg, 53% yield) as a white solid. [M+H]+=514.3, $^1$H NMR (400 MHz, MeOH-d$_4$) δ 7.92 (2 H, d, J=8.35 Hz), 7.67 (2 H, d, J=8.35 Hz), 7.63 (1H, d, J=7.47 Hz), 7.57-7.61 (1 H, m), 7.45 (1 H, t, J=7.91Hz), 7.27 (1 H, dd, J=8.35, 1.76 Hz), 7.11 (1 H, s), 3.89-4.00 (1 H, m), 3.10 (3 H, s), 2.13-2.27 (1 H, m), 1.75-1.90 (3 H, m), 1.58-1.74 (3 H, m), 1.45-1.58 (2 H, m), 1.09-1.26 (2 H, m)

Examples 22 AND 23

The following Examples were prepared using the appropriately substituted aromatic/heteroaromatic alcohols according to the general procedure described for the synthesis of Example 3.

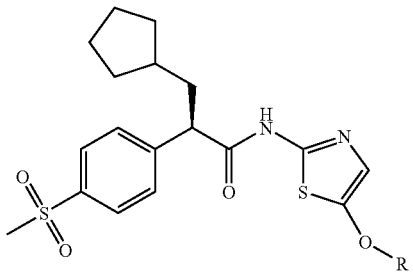

| Example No. | R | [M + H]+ | 1H NMR (400 MHz, CD3OD) | Physical Description & Yield |
|---|---|---|---|---|
| 22 | ![Cl-substituted benzoic acid] | 549.1 | δ 8.08 (2 H, d, J = 1.76 Hz), 7.87-7.96 (3 H, m), 7.66 (2 H, d, J = 8.35 Hz), 7.17 (1 H, s), 7.16 (1 H, d), 3.94 (1 H, t, J = 7.69 Hz), 3.09 (3 H, s), 2.12-2.29 (1 H, m), 1.74-1.91 (3 H, m), 1.57-1.73 (3 H, m), 1.44-1.57 (2 H, m), 1.09-1.26 (2 H, m) | white solid, 7.0 mg (15% yield) |
| 23 | ![F-substituted benzoic acid] | 533.2 | δ 7.92 (2 H, d, J = 8.35 Hz), 7.67 (2 H, d, J = 8.35 Hz), 7.41-7.52 (2 H, m), 7.16 (1 H, s), 7.05-7.13 (1 H, m), 3.95 (1 H, t, J = 7.69 Hz), 3.09 (3 H, s), 2.10-2.27 (1 H, m), 1.74-1.92 (3 H, m), 1.57-1.73 (3 H, m), 1.43-1.57 (2 H, m), 1.08-1.26 (2 H, m) | white solid, 26 mg (74% yield) |

Example 24

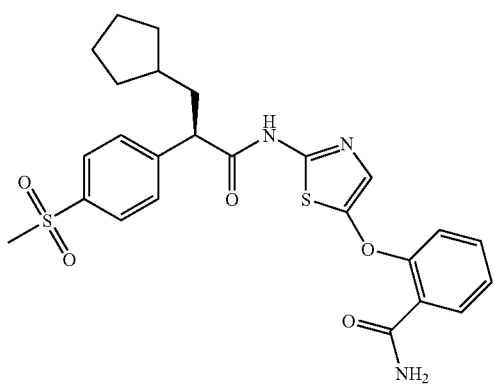

The title compound (2.0 mg, 7% yield, white solid) was prepared from 2-cyanophenol employing the same procedure set forth in Example 21. [M+H]+=514.2, 1H NMR (400 MHz, MeOH-d4) δ 7.91 (2 H, d, J=8.35 Hz), 7.79 (1 H, d, J=6.15 Hz), 7.65 (2 H, d, J=8.35 Hz), 7.40-7.49 (1 H, m), 7.21 (1 H, t, J=7.69 Hz), 7.11 (1 H, s), 7.09 (1 H, d, J=8.79 Hz), 3.87- 3.98 (1 H, m), 3.09 (3 H, s), 2.11-2.26 (1 H, m), 1.74-1.90 (3 H, m), 1.56-1.72 (3 H, m), 1.43-1.56 (2 H, m), 1.08-1.26 (2 H, m).

Assays for Glucokinase Activation

The compounds of formula I of the invention activate glucokinase. Assays which may be used in testing the compounds of formula I of the invention in activating glucokinase are known in the art such as disclosed in U.S. Pat. Nos. 6,320,050, 6,384,200 and 6,610,846 and WO 2004/052869 and in Castellano, A. L., Dong, H., Fyfe, M. C. T., Gardner, L. S., Kamikozawa, Y. et al. (2005) "Glucokinase activating ureas", Bioorg. Med. Chem. Letters, 15:1501-1504, and Grimsby, J., Sarabu, R., Corbett, W. L., Haynes, N-E., Bizzarro, F. T., Coffey, J. W., Guertin, K. R., Hilliard, D. W., Kester, R. F., Mahaney, P. E., Marcus, L., Qi, L., Spence, C. L., Tengi, J., Magnuson, M. A., Chu, C. A., Dvorozniak, M. T., Matschinsky, F. M., Grippo, J. F. (2003) "Allosteric Activators of Glucokinase: Potential Role in Diabetes Therapy", Science, 301:370-373.

In general, compounds of the present invention, such as particular compounds disclosed in the following examples, have been identified to enhance the activity of glucokinase at concentrations equivalent to, or more potently than, 100 μM, preferably 10 μM, more preferably 1 μM, thereby demonstrating compounds of the present invention as especially effective enhancers of activity of glucokinase. Potencies can be calculated and expressed as either $EC_{50}$ (concentration to achieve 50% of full activation) and/or the maximum percentage activation above background, and refer to activity measured employing the assay system described above.

Compounds of formula I of the invention, including compounds described in the Examples hereof, have been tested in the following assay and have shown to be activators of glucokinase.

Biological Data

A tandem Glucokinase activation assay (uncoupled) was used to assess the activity of glucokinase (GK) in the presence of GK activator compounds. The below-described tandem assay protocol was followed using a range of activator compound concentrations from 0 to 100 gM at 5 and 12 mM concentrations of glucose. Human full-length GK (15 nM) was incubated with 5 or 12 mM glucose in 384 well black microtiter plates with a clear bottom. To initiate the GK reaction, magnesium-ATP (3 mM final concentration) was added to the protein in buffer, under the final buffer conditions of 25 mM HEPES buffer, pH 7.1, containing 1 mM DTT (dithiothreitol) and ~5% DMSO. The total reaction volume was 20 μL. The reaction was allowed to proceed for ten minutes and was then quenched with 5 μL EDTA (ethylenediamine tetra-acetic acid; 45 mM final). The components of the detection reaction, ThioNAD (thio-nicotinamide adenine dinucleotide) and G6PDH (glucose-6-phosphate dehydrogenase) (final concentrations of 650 μM and 3.33 Units, respectively), were then added together in a volume of 25 μL, and a total volume of 50 μL. Absorbance was read and activation calculated as a percentage of background activity, ie., GK in the presence of DMSO, with background glucose-6-phosphate subtracted. Absorbance measurements were made at 405 nm on a Spectramax Plus 384 absorbance plate reader (Molecular Devices). Background glucose-6-phosphate was determined by pre-quenching GK with EDTA prior to reaction initiation with ATP.

Expression and Purification of Human GK

Full-length human hepatic GK (untagged) as expressed in BL21 STAR (DE3)pLysS cells (Invitrogen) at 25° C. as described by Mookhtiar et al.[1] The protein was purified essentially as described by Lange[2] with a slight modification. Cell pellets were lysed via three rounds of freezing and thawing, centrifuged at 15000 g for clarification, and precipitated with 40-65% $(NH_4)_2SO4$. The resulting pellet was re-suspended in buffer dialyzed, and applied directly to a Q-Sepharose (Sigma) column followed by elution with a linear 100-600 mM KCl gradient. GK containing fractions were pooled, dialyzed overnight vs. 25 mM HEPES pH 7.2/1 mM $MgCl_2$/1 mM EDTA/0.1 M KCl/1 mM DTT, then dialyzed again with the same buffer with 10% glycerol added.

[1]Mookhtiar, K. A., Kalinowski, S. S., Brown, K. S., Tsay, Y. H., Smith-Monroy, C., and Robinson, G. W. (1996) "Heterologous expression and characterization of rat liver glucokinase regulatory protein", Diabetes 45:1670-1677.
[2]Lange, A. J., Xu, L. Z., Van Poelwijk, F., Lin, K., Granner, D. K., and Pilkis, S. J. (1991) "Expression and site-directed mutagenesis of hepatic glucokinase", Biochem. J., 277:159-163.

Biological data for select Examples are shown in the table below.

| Example No. | $EC_{50}$ with Human Glucokinase @ 12 mM Glucose |
|---|---|
| 19 | 38 |
| 18 | 39 |
| 8 | 753 |
| 21 | 858 |
| 24 | 3958 |
| 20 | 8702 |

In Vivo Studies: Oral Glucose Tolerance Test (OGTT)

Oral glucose tolerance tests were carried out on male DIO (diet-induced obese C57BL/6J mice fed a high fat diet (60% kcal from fat) for 26 weeks prior to experimentation. Mice were fasted overnight before use for experiments. A test compound or vehicle (10% dimethyl acetamide+10% ethanol+ 10% Cremophore+70% water) was given orally 60 min before oral administration of a glucose solution at a dose of 2 g/kg body weight (oral glucose tolerance test; OGTT). Blood glucose levels were measured from tail-bled samples taken at different time points before and after administration of glucose (time course of 2 hours). A time curve of the blood glucose was generated and the change from baseline area-under-the curve (ΔAUC) from 0-120 min was calculated (the time glucose administration being time zero). Example 9 reduced glucose AUC levels in an OGTT test in DIO mice as described above by 37% at a 60 mg/kg dose.

What is claimed is:
1. A compound having the structure

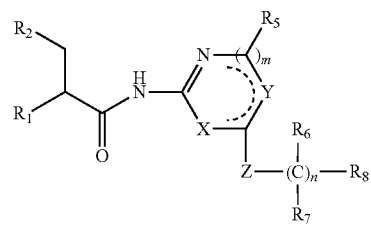

wherein
⁀ in the ring represents one or two double bonds;
$R_1$ is selected from the group consisting of aryl and heteroaryl;
$R_2$ is selected from the group consisting of cycloalkyl and heterocyclyl;
X is S;
Y is $CR_4$;
Z is selected from the group consisting of
O,
S,
S(O),
$S(O)_2$, and
$NR_{5a}$;
$R_4$ and $R_5$ are the same or different and are independently selected from the group consisting of
H,
halogen,
alkyl,
aryl,
heteroaryl,
alkylaryl, and
alkylheteroaryl
$R_{5a}$ is selected from the group consisting of
H,
alkyl, and
aryl;

R$_6$ and R$_7$ are the same or different and are independently selected from the group consisting of
- H,
- halogen, and
- alkyl;

R$_8$ is selected from the group consisting of
- optionally substituted aryl, and
- optionally substituted heteroaryl;

m is 0;
n is 0, 1, 2, or 3;
stereoisomers thereof, or a pharmaceutically acceptable salt thereof;
with the proviso that
where Z is S, S(O) or S(O)$_2$, then R$_8$ must be substituted with a substituent selected from
1) —C(O)NR$^f$R$^g$;
2) —NHC(O)OR$^h$;
3) —OC(O)NHR$^h$;
4) alkoxy;
5) tetrazolyl; and
6) SO$_2$NR$^i$R$^j$;

where R$^f$ and R$^g$ are independently selected from H, alkyl and aryl or R$^f$ and R$^g$ can be taken together with the N atom to which they are attached to form a 3 to 7 membered heterocyclo ring;
R$^h$ is alkyl or aryl; and
R$^i$ and R are independently selected from H, alkyl and aryl;
provided that at least one of R$^i$ and R$^j$ is other than H.

2. The compound as defined in claim 1 wherein Y is CH.
3. The compound as defined in claim 1 wherein Z is O or NR$_{5a}$.
4. The compound as defined in claim 3 wherein Z is O.
5. The compound as defined in claim 1 wherein
R$_1$ is aryl or alkylsulfonylaryl;
R$_2$ is cycloalkyl;
Z is O, S, or SO$_2$;
n is 0 or 1;
R$_6$ and R$_7$ are each hydrogen; and
R$_8$ is phenyl or heteroaryl,
wherein R$_8$ is substituted with —C(O)NR$^f$R$^g$, —NHC(O)OR$^h$, —OC(O)NHR$^h$, alkoxy, tetrazolyl or —SO$_2$NR$^i$R$^j$.

6. The compound as defined in claim 1 wherein
R$_1$ is

R$_2$ is

R$_4$ is H;
Z is S, O, or SO$_2$;

is CH$_2$ or a bond; and
R$_8$ is heteroaryl or phenyl,
wherein R$_8$ is substituted with —C(O)NR$^f$R$^g$, —NHC(O)OR$^h$, —OC(O)NHR$^h$, alkoxy, tetrazolyl or —SO$_2$NR$^i$R$^j$,
where R$^f$ and R$^g$ are independently selected from H, alkyl and aryl or R$^f$ and R$^g$ can be taken together with the N atom to which they are attached to form a 3 to 7 membered heterocyclo ring.

7. The compound as defined in claim 1 wherein R$_8$ is

8. The compound as defined in claim 1 which is

73
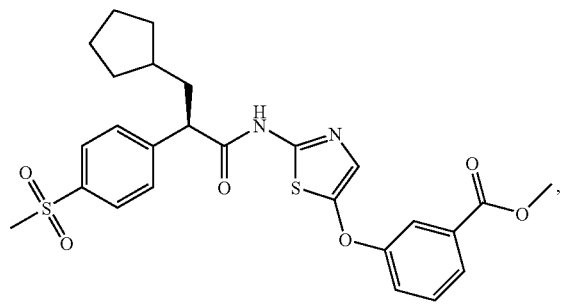
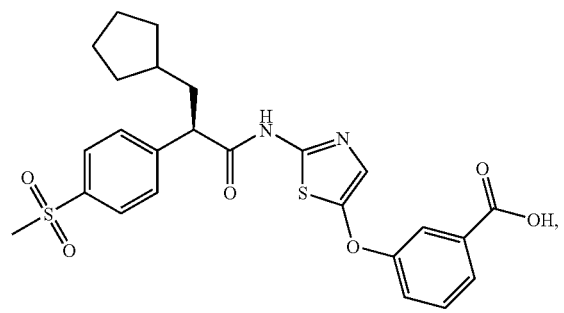
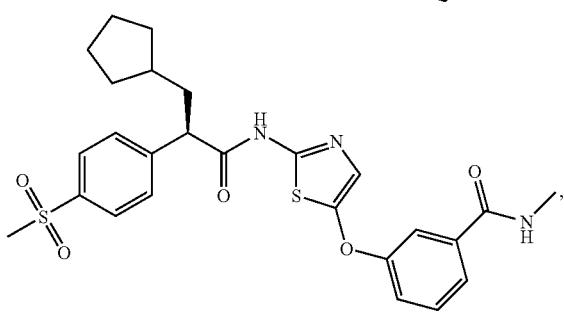
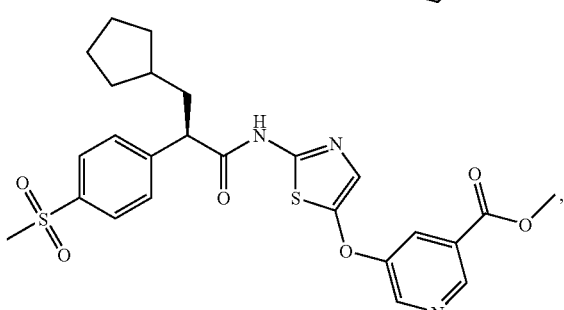
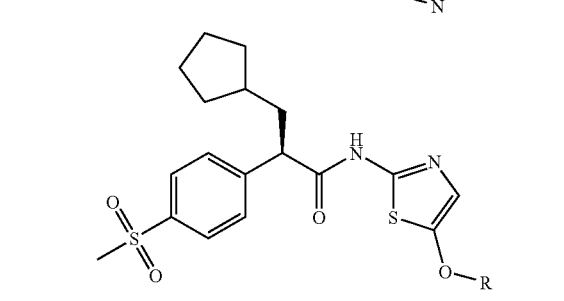
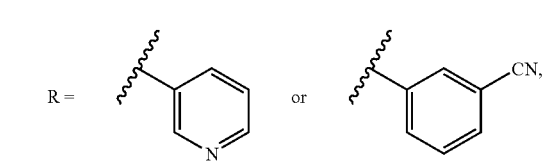
74
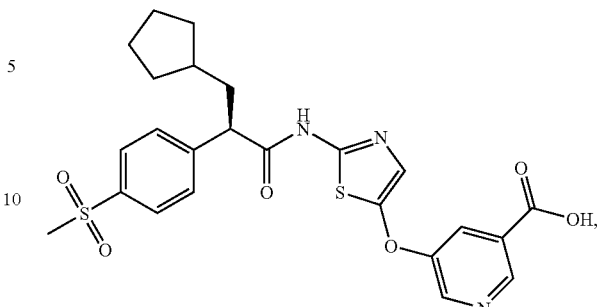
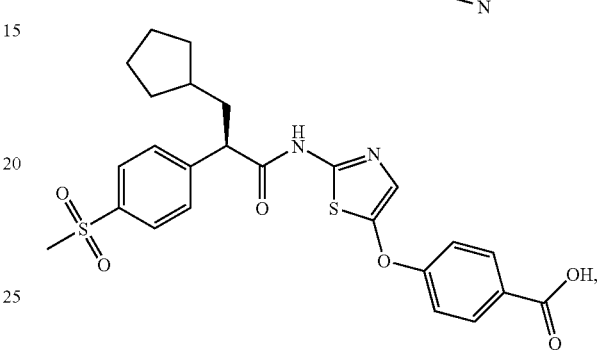
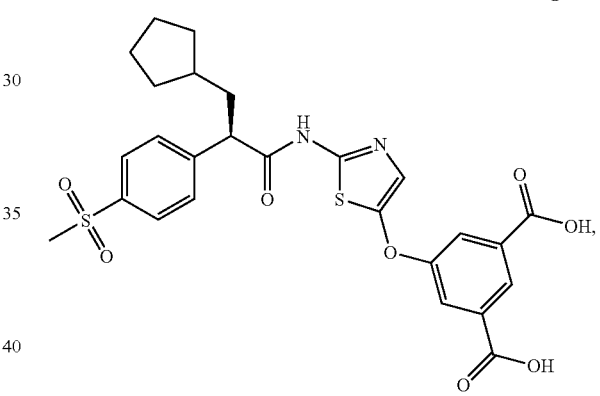
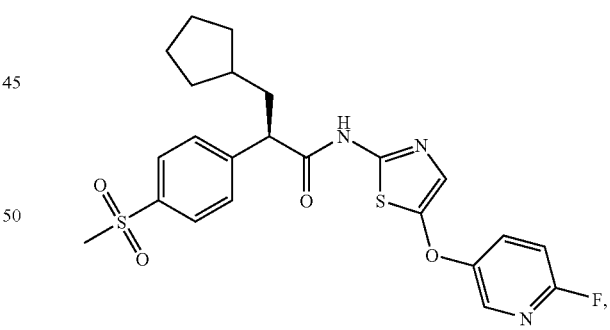
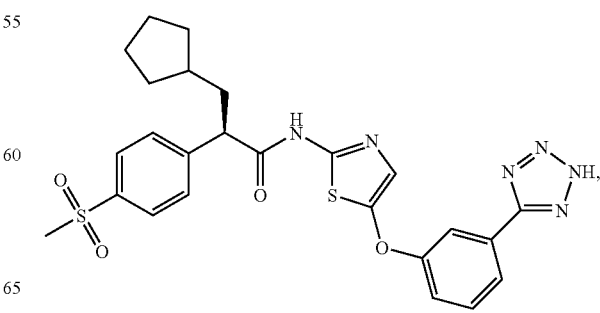

-continued
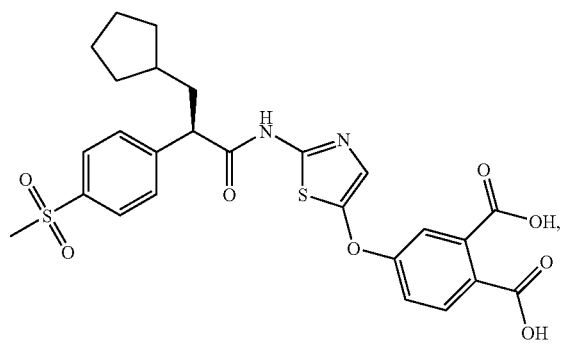
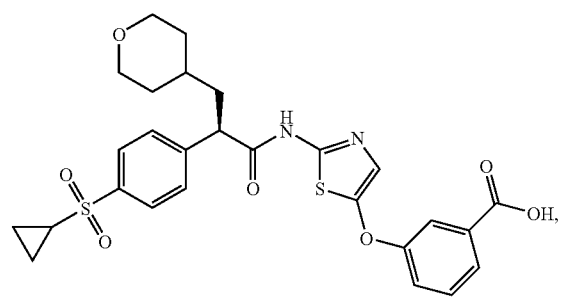
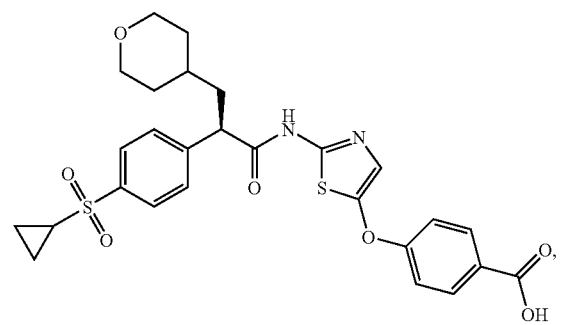
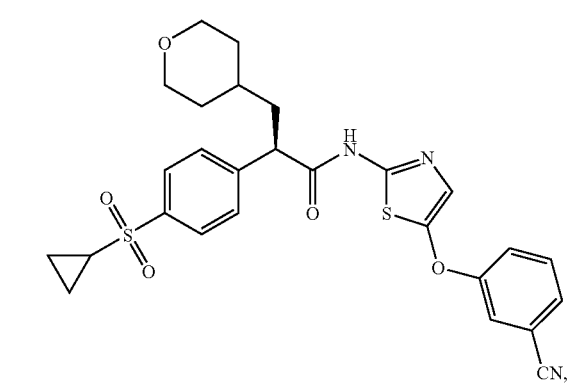
-continued
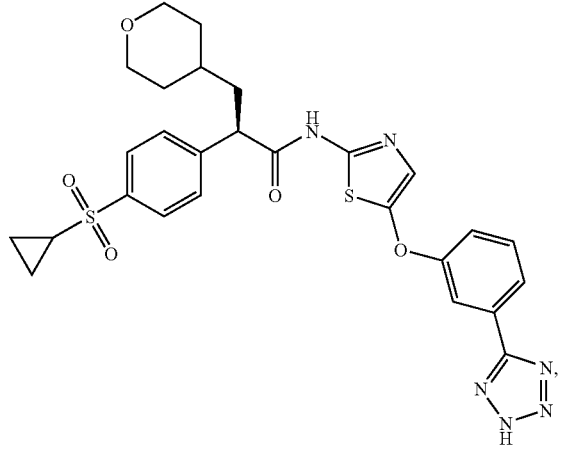
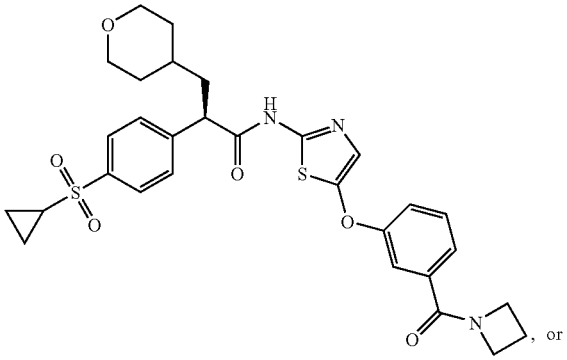
, or
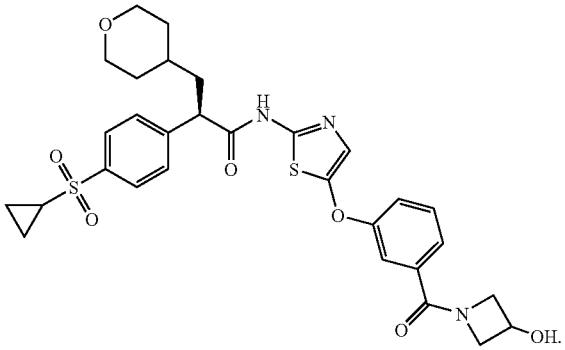
9. The compound as defined in claim 1 which is
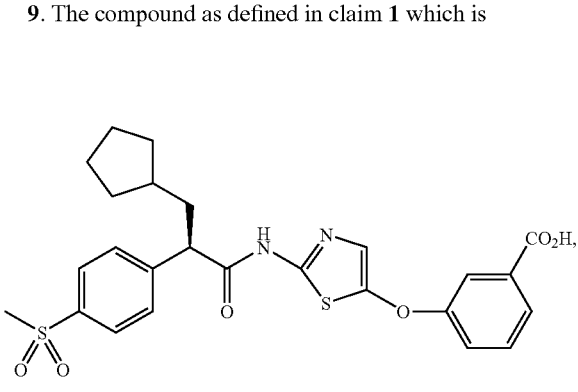

-continued

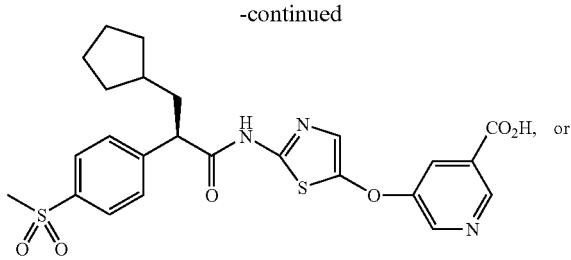

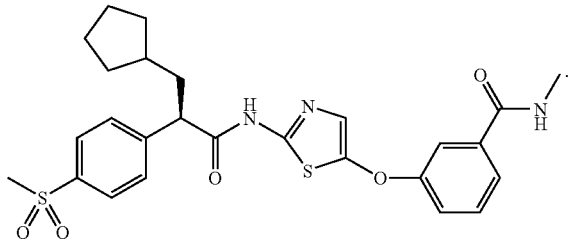

10. A compound having the structure

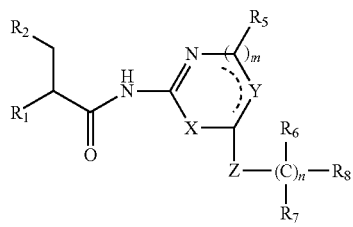

wherein
⌒ in the ring represents one or two double bonds;
$R_1$ is selected from the group consisting of aryl and heteroaryl;
$R_2$ is selected from the group consisting of cycloalkyl and heterocyclyl;
X is S;
Y is $CR_4$;
Z is selected from the group consisting of
O and $NR_{5a}$;
$R_4$ and $R_5$ are the same or different and are independently selected from the group consisting of
H,
halogen,
alkyl,
aryl,
heteroaryl,
alkylaryl, and
alkylheteroaryl
$R_{5a}$ is selected from the group consisting of
H,
alkyl, and
aryl;
$R_6$ and $R_7$ are the same or different and are independently selected from the group consisting of
H,
halogen, and
alkyl;
$R_8$ is selected from the group consisting of
aryl, and
heteroaryl, wherein $R_8$ is substituted with —C(O)$NR^fR^g$, —NHC(O)$OR^h$, —OC(O)$NHR^h$, alkoxy, tetrazolyl or —$SO_2NR^iR^j$,
where $R^f$ and $R^g$ are independently selected from H, alkyl and aryl or $R^f$ and $R^g$ can be taken together with the N atom to which they are attached to form a 3 to 7 membered heterocyclo ring;
m is 0 or 1; and
n is 0, 1, 2, or 3;
and stereoisomers thereof, or a pharmaceutically acceptable salt thereof

11. The compound as defined in claim 10 having the structure

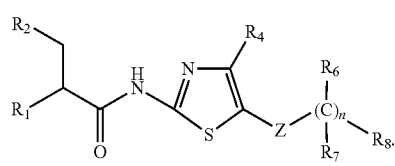

12. The compound as defined in claim 10 wherein $R_4$ is H.
13. The compound as defined in claim 11 wherein
$R_1$ is aryl or alkylsulfonylaryl;
$R_2$ is cycloalkyl;
Z is O;
n is 0 or 1;
$R_6$ and $R_7$ are each hydrogen; and
$R_8$ is phenyl or heteroaryl,
wherein $R_8$ is substituted with —C(O)$NR^fR^g$, —NHC(O)$OR^h$, —OC(O)$NHR^h$, alkoxy, tetrazolyl or —$SO_2NR^iR^j$.
14. The compound as defined in claim 10 wherein
$R_1$ is

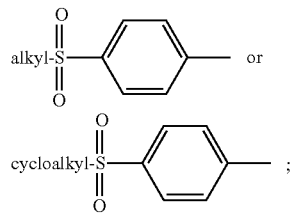

$R_2$ is

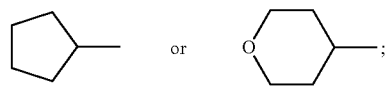

$R_4$ is H;
m is 0;
Z is O;

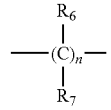

is $CH_2$ or a bond; and
$R_8$ is heteroaryl or phenyl.

15. The compound as defined in claim 14 wherein R_8 is

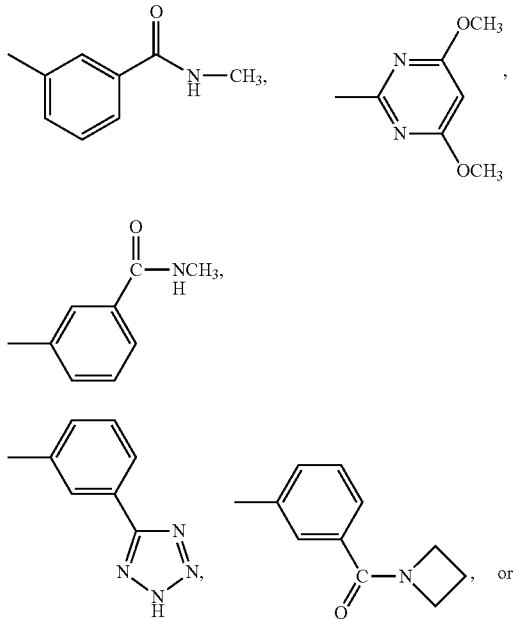

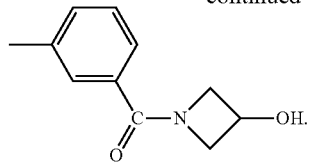

16. A pharmaceutical composition comprising a compound as defined in claim 1 and a pharmaceutically acceptable carrier thereof.

17. A pharmaceutical composition comprising a compound as defined in claim 1 and another therapeutic agent which is an anti-diabetic agent, anti-hyperglycemic agent, anti-hyperinsulinemic agent, anti-retinopathic agent, anti-neuropathic agent, anti-nephropathic agent, anti-atherosclerotic agent, anti-infective agent, anti-ischemic agent, anti-hypertensive agent, anti-obesity agent, anti-dyslipidemic agent, anti-hyperlipidemic agent, anti-hypertriglyceridemic agent, anti-hypercholesterolemic agent, anti-ischemic agent, anti-cancer agent, anti-cytotoxic agent, anti-restenotic agent, anti-pancreatic agent, lipid lowering agent, appetite suppressant, memory enhancing agent, or cognitive agent.

18. A method of treating Type II diabetes, which comprises administering to a patient in need of treatment a therapeutically effective amount of a compound as defined in claim 1.

* * * * *

UNITED STATES PATENT AND TRADEMARK OFFICE
CERTIFICATE OF CORRECTION

PATENT NO. : 7,888,504 B2  
APPLICATION NO. : 11/769799  
DATED : February 15, 2011  
INVENTOR(S) : Chen et al.

Page 1 of 1

It is certified that error appears in the above-identified patent and that said Letters Patent is hereby corrected as shown below:

On Title Page:

Col. 2 (Other Publications), line 3, delete "Pharmaceutices," and insert -- Pharmaceutics, --, therefor;

Col. 2 (Other Publications), line 10, delete "Anstract" and insert -- Abstract --, therefor;

Col. 2 (Abstract), line 12, delete "$N_4$;" and insert -- $NR_4$; --, therefor;

Claim 1, col. 71, line 29, delete "R" and insert -- $R^j$ --, therefor; and

Claim 10, col. 78, line 11, delete "thereof" and insert -- thereof. --, therefor.

Signed and Sealed this  
Twenty-fifth Day of October, 2011

David J. Kappos  
*Director of the United States Patent and Trademark Office*